(12) United States Patent
Blonshine et al.

(10) Patent No.: US 11,752,108 B2
(45) Date of Patent: Sep. 12, 2023

(54) GOLD PARTICLES INCLUDING AN OLEO-GUM RESIN AND/OR A DERIVATIVE THEREOF AND METHODS OF PREPARING AND USING THE SAME

(71) Applicants: Todd Elliot Blonshine, Cary, NC (US); James Ralph Compton, New Hill, NC (US)

(72) Inventors: Todd Elliot Blonshine, Cary, NC (US); James Ralph Compton, New Hill, NC (US)

( * ) Notice: Subject to any disclaimer, the term of this patent is extended or adjusted under 35 U.S.C. 154(b) by 0 days.

(21) Appl. No.: 17/203,138

(22) Filed: Mar. 16, 2021

(65) Prior Publication Data
US 2021/0205231 A1 Jul. 8, 2021

Related U.S. Application Data

(63) Continuation-in-part of application No. PCT/US2020/051189, filed on Sep. 17, 2020.

(60) Provisional application No. 62/901,550, filed on Sep. 17, 2019.

(51) Int. Cl.
*A61K 9/51* (2006.01)
*A61K 36/324* (2006.01)
*A61K 36/328* (2006.01)

(52) U.S. Cl.
CPC .......... *A61K 9/5115* (2013.01); *A61K 9/5192* (2013.01); *A61K 36/324* (2013.01); *A61K 36/328* (2013.01)

(58) Field of Classification Search
None
See application file for complete search history.

(56) References Cited

U.S. PATENT DOCUMENTS

| | | | |
|---|---|---|---|
| 4,501,729 A | 2/1985 | Boucher et al. | |
| 9,795,634 B1 * | 10/2017 | Moses | A61K 45/06 |
| 2009/0136595 A1 | 5/2009 | Shah et al. | |
| 2016/0158261 A1 | 6/2016 | Friedman et al. | |
| 2019/0142734 A1 | 5/2019 | Florence et al. | |

FOREIGN PATENT DOCUMENTS

| | | |
|---|---|---|
| JP | 2009240951 A | 10/2009 |
| WO | 2021055550 A1 | 3/2021 |

OTHER PUBLICATIONS

Assefa, A.G., et al., Microwave-Assisted Green Synthesis of Gold Nanoparticles Using Olibanum Gum (*Boswellia serrate*) and its Catalytic Reduction of 4-Nitrophenol and Hexacyanoferrate (III) by Sodium Borohydride, J Clust Sci (2017) 28:917-935 (Year: 2017).*

Cao, B., et al., "Seeing the Unseen of the Combination of Two Natural Resins, Frankincense and Myrrh: Changes in Chemical Constituents and Pharmacological Activities", Molecules, 24(3076):1-27(2019).*

Chou et al. "Quantitative Analysis of Dose-Effect Relationships: The Combined Effects of Multiple Drugs or Enzyme Inhibitors" Advances in Enzyme Regulation, 22:27-55 (1984).

Gonda, I "Aerosols for delivery of therapeutic and diagnosticagents to the respiratory tract" Critical Reviews in Therapeutic Drug Carrier Systems, 6:273-313 (1990) (Abstract only).

Holford et al. "Understanding the Dose-Effect Relationship" Clinical Pharmacokinetics, 6:429-453 (1981) (Abstract only).

International Search Report and the Written Opinion of the International Searching Authority corresponding to International Patent Application No. PCT/US2020/051189 (11 pages) (dated Sep. 17, 2020).

Katti et al. "Green Nanotechnology from Cumin Phytochemicals: Generation of Biocompatible Gold Nanoparticles" International Journal of Green Nanotechnology: Biomedicine, 1(1):B39-B52 (2009).

Raeburn et al. "Techniques for drug delivery to the airways, and the assessment of lung function in animal models" Journal of Pharmacological and Toxicological Methods, 27(3):143-159 (1992) (Abstract only).

Shukla et al. "Soybeans as a Phytochemical Reservoir for the Production and Stabilization of Biocompatible Gold Manoparticles" Small, 4(9):1425-1436 (2008).

Tyle, Praveen "Iontophoretic Devices for Drug Delivery" Pharmaceutical Research, 3(6):318-326 (1986).

Cao et al. "Seeing the Unseen of the Combination of Two Natural Resins, Frankincense and Myrrh: Changes in Chemical Constituents and Pharmacological Activities" Molecules, 24(3076):1-27 (2019).

* cited by examiner

*Primary Examiner* — H. Sarah Park
(74) *Attorney, Agent, or Firm* — Myers Bigel, P.A.

(57) ABSTRACT

Described herein are particles including gold and an oleo-gum resin and/or a derivative of an oleo-gum resin. The particles may be gold nanoparticles and the oleo-gum resin may be frankincense and/or myrrh. Also described herein are methods of preparing such particles, compositions including such particles and methods of using particles and compositions of the present invention.

17 Claims, 6 Drawing Sheets

GOLD PARTICLES INCLUDING AN OLEO-GUM RESIN AND/OR A DERIVATIVE THEREOF AND METHODS OF PREPARING AND USING THE SAME

RELATED APPLICATION INFORMATION

This application claims the benefit of and priority to International Application No. PCT/US2020/051189, filed Sep. 17, 2020, which claims priority to U.S. Application Ser. No. 62/901,550, filed Sep. 17, 2019, the disclosure of each of which is incorporated herein by reference in its entirety.

FIELD

The present invention relates to gold particles that include an oleo-gum resin and/or a derivative thereof and to methods of using and preparing such particles.

BACKGROUND

Natural products such as herbs have been used for their medicinal benefits for years. However, the effectiveness of such natural products is often small and could be improved to make the benefits medically significant.

SUMMARY

A first aspect of the present invention is directed to a particle comprising gold and an oleo-gum resin and/or a derivative thereof. In some embodiments, the particle is a gold nanoparticle.

Another aspect of the present invention is directed to a composition comprising a particle including gold and an oleo-gum resin and/or a derivative thereof.

A further aspect of the present invention is directed to a method of making a particle, the method comprising: combining an oleo-gum resin and/or a derivative thereof and a solution comprising soluble gold to form a mixture; and forming a particle from the mixture, wherein the particle comprises gold and the oleo-gum resin and/or a derivative thereof.

It is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim and/or file any new claim accordingly, including the right to be able to amend any originally filed claim to depend from and/or incorporate any feature of any other claim or claims although not originally claimed in that manner. These and other objects and/or aspects of the present invention are explained in detail in the specification set forth below. Further features, advantages and details of the present invention will be appreciated by those of ordinary skill in the art from a reading of the figures and the detailed description of the preferred embodiments that follow, such description being merely illustrative of the present invention.

DETAILED DESCRIPTION OF EXAMPLE EMBODIMENTS

Figure 1:
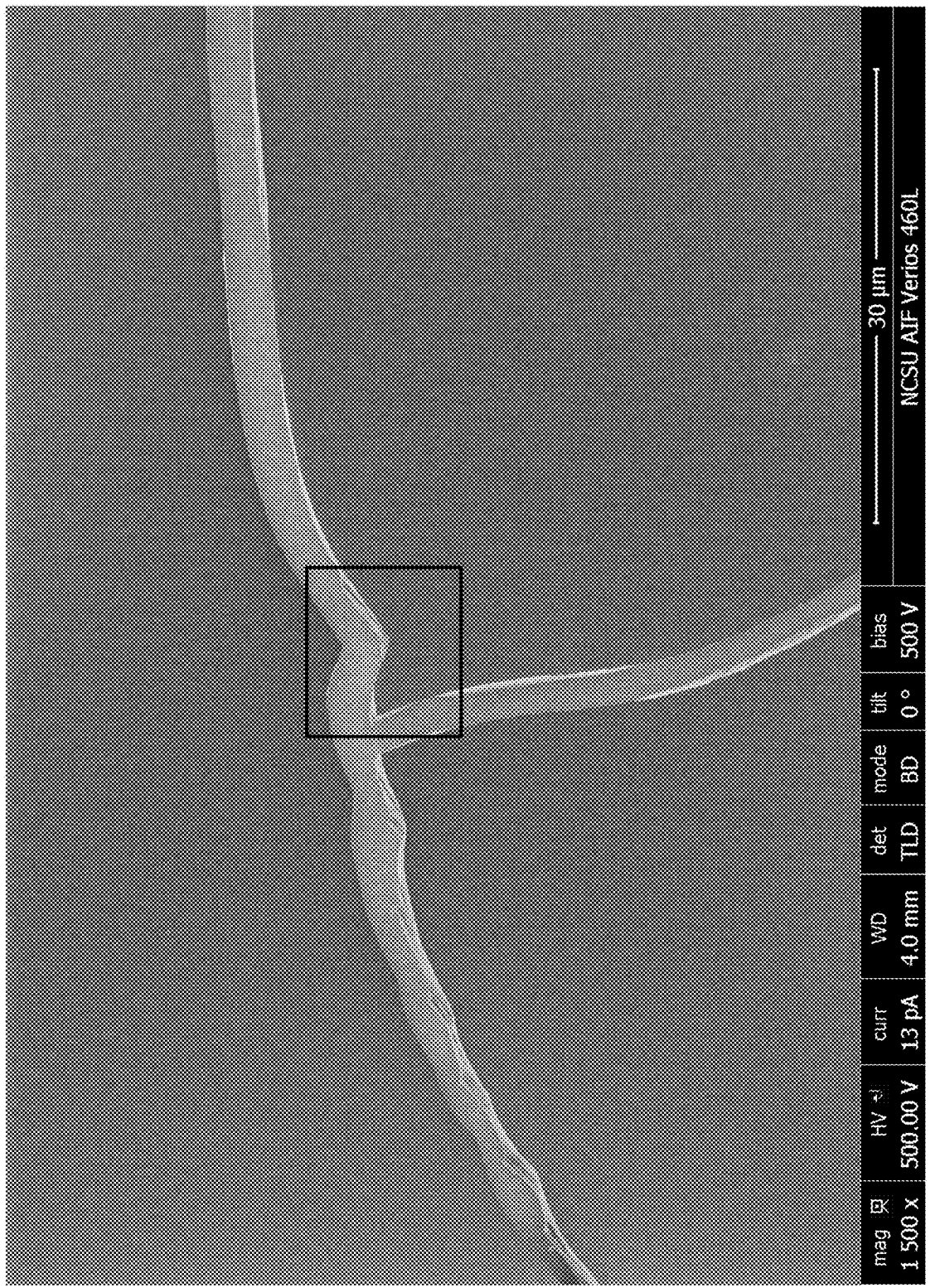
FIGS. 1-6 are scanning electron microscope images of various samples according to embodiments of the present invention.

The present invention is now described more fully hereinafter in which embodiments of the invention are described. This invention may, however, be embodied in many different forms and should not be construed as limited to the embodiments set forth herein; rather these embodiments are provided so that this disclosure will be thorough and complete and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a," "an" and "the" are intended to include the plural forms as well, unless the context clearly indicates otherwise.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. The terminology used in the description of the invention herein is for the purpose of describing particular embodiments only and is not intended to be limiting of the invention. All publications, patent applications, patents and other references mentioned herein are incorporated by reference in their entirety. In case of a conflict in terminology, the present specification is controlling.

Also as used herein, "and/or" refers to and encompasses any and all possible combinations of one or more of the associated listed items, as well as the lack of combinations when interpreted in the alternative ("or").

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed.

As used herein, the transitional phrase "consisting essentially of" (and grammatical variants) is to be interpreted as encompassing the recited materials or steps "and those that do not materially affect the basic and novel characteristic(s)" of the claimed invention. See, In re Herz, 537 F.2d 549, 551-52, 190 U.S.P.Q. 461, 463 (CCPA 1976) (emphasis in the original); see also MPEP § 2111.03. Thus, the term "consisting essentially of" as used herein should not be interpreted as equivalent to "comprising."

The term "about," as used herein when referring to a measurable value such as an amount or concentration and the like, is meant to encompass variations of ±10%, ±5%, ±1%, ±0.5%, or even ±0.1% of the specified value as well as the specified value. For example, "about X" where X is the measurable value, is meant to include X as well as variations of ±10%, ±5%, ±1%, ±0.5%, or even ±0.1% of X. A range provided herein for a measurable value may include any other range and/or individual value therein.

As used herein, the terms "increase," "increases," "increased," "increasing," and similar terms indicate an elevation in the specified parameter or value of at least about 5%, 10%, 15%, 20%, 25%, 30%, 35%, 40%, 45%, 50%, 55%, 60%, 65%, 70%, 75%, 80%, 85%, 90%, 95%, 100%, 150%, 200%, 300%, 400%, 500% or more.

As used herein, the terms "reduce," "reduces," "reduced," "reduction," "inhibit," and similar terms refer to a decrease in the specified parameter or value of at least about 5%, 10%, 15%, 20%, 25%, 30%, 35%, 40%, 45%, 50%, 55%, 60%, 65%, 70%, 75%, 80%, 85%, 90%, 95%, 97%, or 100%.

Provided according to embodiments of the present invention are particles comprising gold and an oleo-gum resin or a derivative thereof. A particle of the present invention has a spherical shape (e.g., a roughly spherical shape) or may be in the form of a tube or fiber. In some embodiments, a particle of the present invention is a nanoparticle. "Nanoparticle" as used herein refers to a particle having at least one dimension that is at least 1 nm and less than 1000 nm. In some embodiments, a particle of the present invention has a diameter of about 1, 2, 5, 10, 15, 20, or 25 nm to about 30, 35, 40, 45, 50, 55, 60, 65, 70, 75, 80, 85, 90, 100, 250, 500, 750, or 1000 nm. In some embodiments, a particle of the present invention has a diameter of about 1, 5, 10, 15, 20, 25, 30, 35, 40, 45, 50, 55, 60, 65, 70, 75, 80, 85, 90, 100, 150, 200, 250, 300, 350, 400, 450, 500, 600, 700, 800, 900, or 1000 nm. In some embodiments, a particle of the present invention has a diameter of about 30, 35, or 40 nm to about 45, 50, 55, 60, 65, 70, 75, 80, 85, 90, or 100 nm. In some embodiments, a particle of the present invention has a diameter of at least 30 nm. The diameter of respective particles of the present invention in a plurality of particles may vary by about ±50%, 40%, 30%, 20%, 15%, 10%, 5%, or 1%, or less. In some embodiments, the diameter of the respective particles in the plurality of particles may vary by about ±20% or less (e.g., by about ±15%, 10%, 5%, or 1%, or less). In some embodiments, particles of the present invention are monodisperse. In some embodiments, particles of the present invention are polydisperse. In some embodiments, the average diameter of a plurality of particles of the present invention is about 1, 2, 5, 10, 15, 20, or 25 nm to about 30, 35, 40, 45, 50, 55, 60, 65, 70, 75, 80, 85, 90, 100, 250, 500, 750, or 1000 nm. In some embodiments, the average diameter of a plurality of particles of the present invention is about 1, 5, 10, 15, 20, 25, 30, 35, 40, 45, 50, 55, 60, 65, 70, 75, 80, 85, 90, 100, 150, 200, 250, 300, 350, 400, 450, 500, 600, 700, 800, 900, or 1000 nm. In some embodiments, the average diameter of a plurality of particles of the present invention is about 30, 35, or 40 nm to about 45, 50, 55, 60, 65, 70, 75, 80, 85, 90, or 100 nm. In some embodiments, the average diameter of a plurality of particles of the present invention is at least 30 nm. A particle of the present invention may be a nanosphere, nanocapsule, nanorod, nanofiber, nanoshell, nanotube, nanoprism, nanocluster, nanocage, or nanostar, optionally a gold nanoparticle such as a gold nanosphere, gold nanorod, gold nanoshell, gold nanoprism, gold nanocluster, gold nanocage, or gold nanostar. In some embodiments, a particle of the present invention is a nanofiber, nanotube, or a nanorod that optionally has a diameter or width of about 30, 35, or 40 nm to about 45, 50, 55, 60, 65, 70, 75, 80, 85, 90, or 100 nm and a length of about 1, 2, 5, 10, 15, 20, 25, or 30 nm to about 35, 40, 45, 50, 55, 60, 65, 70, 75, 80, 85, 90, or 100 nm. When the particle is a nanofiber, the length of the particle may be greater than 100 nm (e.g., 250, 500, or 1000 nm or more). In some embodiments, a particle of the present invention may have a diameter and/or width of about 20, 21, 22, 23, 24, 25, 26, 27, 28, 29, 30, 31, 32, 33, 34, 35, 36, 37, 38, 39, or 40 nm to about 41, 42, 43, 44, 45, 46, 47, 48, 49, 50, 51, 52, 53, 54, or 55 nm. In some embodiments, a particle of the present invention may have a length and a width that is at least 30 nm (e.g., about 35, 40, 45, 50, 55, 60, 65, 70, 75, 80, 85, 90, or 100 nm). The particle may be a colloidal particle (e.g., a colloidal nanoparticle).

A particle of the present invention may comprise a core having an outer surface. The core may comprise gold and/or an oleo-gum resin or a derivative thereof. Gold may make up and/or form the core of the particle and the oleo-gum resin or derivative thereof may be present in and/or on the core. In some embodiments, gold and the oleo-gum resin or derivative thereof may make up and/or form the core of the particle. In some embodiments, the core has a diameter of about 1, 2, 5, 10, 15, 20, or 25 nm to about 30, 35, 40, 45, 50, 55, 60, 65, 70, 75, 80, 85, 90, 100, 250, 500, 750, or 1000 nm. In some embodiments, the core has a diameter of about 1, 5, 10, 15, 20, 25, 30, 35, 40, 45, 50, 55, 60, 65, 70, 75, 80, 85, 90, 100, 150, 200, 250, 300, 350, 400, 450, 500, 600, 700, 800, 900, or 1000 nm. In some embodiments, the core comprises gold and the outer surface comprises an oleo-gum resin or a derivative thereof and optionally gold. In some embodiments, the oleo-gum resin or derivative thereof makes up and/or forms the outer surface, and gold may optionally be present in the and/or on the outer surface. In some embodiments, the particle comprises the oleo-gum resin or derivative thereof bound to (e.g., via a covalent and/or noncovalent bond) the core of the particle comprising gold. In some embodiments, the core and/or a gold nanoparticle of the present invention serve as and/or is a carrier for an oleo-gum resin or a derivative thereof. In some embodiments, the particle comprises the oleo-gum resin or derivative thereof bound to (e.g., via a covalent and/or noncovalent bond) gold. An interior and/or exterior surface of a particle of the present invention may directly contact an oleo-gum resin and/or a derivative thereof in that there is no material (e.g., a reducing agent or capping agent such as a citrate ion) between the surface of the particle and the oleo-gum resin and/or a derivative thereof. When two materials are in direct contact, there is no material between the two materials and the two materials may be bound (e.g., covalently and/or noncovalently), adsorbed, adhered together, or associated with each other. In some embodiments, a particle of the present invention is devoid of a gold surface in direct contact with a reducing agent and/or capping agent. In some embodiments, a particle of the present invention is devoid of a gold surface in direct contact with a citrate ion. In some embodiments, a particle of the present invention is devoid of a negatively charged material (e.g., a negatively charged reducing agent, negatively charged capping agent and/or negatively charged ion such as a citrate ion) between a surface of the particle and the oleo-gum resin and/or a derivative thereof and/or between a gold atom and the oleo-gum resin and/or a derivative thereof.

"Oleo-gum resin" as used herein refers to a mixture that is obtained from a natural source (e.g., a tree) and the mixture includes a resin, a gum, and an oil (e.g., a volatile oil and/or non-volatile oil). In some embodiments, an oleo-gum resin is an exudate (e.g., sap and/or pitch) from a natural source such as from the stems, trunk, bark, leaves, and/or branches of the natural source. The exudate may be a solid or liquid. A "raw oleo-gum resin" as used herein refers to an exudate from a natural source that, optionally other than being dried to provide a solid form, is unmodified from its natural state. In some embodiments, the oleo-gum resin is in the form of a powder, particulate, and/or tear (i.e., solidified exudate, optionally in the form of a tear shaped droplet). In some embodiments, an oleo-gum resin may comprise a resin in an amount of about 10%, 15%, 20%, or 25% to about 30%, 40%, 50%, 60%, 70%, or 80% by weight of the oleo-gum resin; a gum in an amount of about 10%, 15%, 20%, or 25% to about 30%, 40%, 50%, 60%, 70%, or 80% by weight of the oleo-gum resin; and an oil an amount of about 1%, 5%, or 10% to about 15%, 20%, or 25% by weight of the oleo-gum resin. A particle of the present invention may comprise one or more (e.g., 1, 2, 3, 4, 5, or more) different oleo-gum resins or derivatives thereof that optionally may be present in and/or on the particle. In some embodiments, a particle of the present invention comprises at least two different oleo-gum resins or derivatives thereof.

An oleo-gum resin may be from (e.g., an exudate of) a tree and/or shrub of the genus selected from the group consisting of *Boswellia, Commiphora,* and any combination thereof. In some embodiments, an oleo-gum resin is from (e.g., an exudate of) a tree of the genus *Boswellia* such as from the species *B. sacra, B. carteri, B. bhaw-dajiana, B. frereana, B. papyrifera, B. serrata, B. dalzielii, B. microphylla, B. ogadensis, B. occulta, B. ameero, B. boranensis, B. bricchettii, B. bullata, B. chariensis, B. dioscoridis, B. elegans, B. elongata, B. globosa, B. hildebrandtii, B. holstii, B. madagascariensis, B. microphylla, B. multifoliolata, B. nana, B. neglecta, B. odorata, B. ogadensis, B. ovalifoliolata, B. pirottae, B. popoviana, B. rivae, B. ruspoliana, B. socotrana,* and any combination thereof. An oleo-gum resin from (e.g., an exudate of) a tree of the genus *Boswellia* is also referred to herein as "frankincense." In some embodiments, an oleo-gum resin from (e.g., an exudate of) a tree of the genus *Boswellia* may comprises a resin in an amount of about 40%, 45%, 50%, or 55% to about 60%, 65%, 70%, 75%, or 80% by weight of the oleo-gum resin; a gum in an amount of about 10%, 15%, or 20% to about 25%, 30%, 35%, 40%, 45%, or 50% by weight of the oleo-gum resin; and an oil an amount of about 1% or 5% to about 10%, 15%, or 20% by weight of the oleo-gum resin. In some embodiments, an oleo-gum resin is from (e.g., an exudate of) a tree and/or shrub of the genus *Commiphora* such as from the species *C. africana, C. alaticaulis, C. angolensis, C. boranensis, C. caudata, C. ciliata, C. confusa, C. corrugata, C. erosa, C. erythraea, C. gileadensis, C. glandulosa, C. guidottii, C. guillauminii, C. habessinica, C. harveyi, C. holtziana, C. humbertii, C. kataf, C. kua, C. madagascariensis, C. monoica, C. mossambicensis, C. myrrha, C. molmol, C. saxicola, C. schimperi, C. simplicifolia, C. sphaerocarpa, C. stocksiana, C. unilobata, C. wightii,* and any combination thereof. In some embodiments, an oleo-gum resin from (e.g., an exudate of) a tree and/or shrub of the genus *Commiphora* may comprises a resin in an amount of about 10%, 15%, or 20% to about 25%, 30%, or 35% by weight of the oleo-gum resin; a gum in an amount of about 40%, 45%, or 50% to about 55%, 60%, 65%, 70%, or 75% by weight of the oleo-gum resin; and an oil an amount of about 1% or 5% to about 10%, 15%, or 20% by weight of the oleo-gum resin. An oleo-gum resin from (e.g., an exudate of) a tree and/or shrub of the genus *Commiphora* is also referred to herein as "myrrh." In some embodiments, an oleo-gum resin (e.g., a raw oleo-gum resin) is selected from frankincense, myrrh, and any combination thereof.

An oleo-gum resin may comprise one or more compound(s) such as organic compounds. A "derivative" as used herein in reference to an oleo-gum resin (e.g., frankincense and/or myrrh) includes one or more compound(s) of an oleo-gum resin and/or one or more compound(s) that are obtained from a reaction involving a compound of an oleo-gum resin. For example, a derivative of an oleo-gum resin may comprise one or more compound(s) of the oleo-gum resin such as one or more compound(s) of the resin, gum and/or oil of the oleo-gum resin. A derivative of an oleo-gum resin may also include one or more compound(s) that are obtained from a reaction in which a compound of the oleo-gum resin is a reactant. Exemplary reactions involving a compound of an oleo-gum resin as a reactant include, but are not limited to, a reaction in which the reactant is heated, optionally in the presence of water and/or soluble gold, to provide a derivative of the oleo-gum resin; a reaction in which the reactant is combined and/or reacted with water to provide a derivative of the oleo-gum resin; and/or a reaction in which the reactant is reacted with another reactant (e.g., a different compound of an oleo-gum resin), optionally in the presence of water and/or soluble gold, to provide a derivative of the oleo-gum resin. In some embodiments, a derivative of an oleo-gum resin is a compound that is soluble in water. In some embodiments, a derivative of an oleo-gum resin is a compound present in the oleo-gum resin (e.g., present in the exudate). Exemplary compounds that may be present in an oleo-gum resin include, but are not limited to, a terpenoid (e.g., a boswellic acid, a monoterpenoid, a diterpenoid, a triterpenoid, sesquiterpenoid, a pentacyclic triterpenoid, a furanosesquiterpenoid, etc.), a steroid (e.g., a natural steroid), a flavonoid, a terpene, a guggulsterol, a guggulsterone, a lignan, a sugar, an amino acid, a polypeptide, a carbohydrate, a fatty alcohol, a fatty ester, a sterol (e.g., a natural sterol), a precursor of any of the foregoing, and any combination thereof. In some embodiments, a particle of the present invention incudes one or more (e.g., 1, 2, 3, 4, or more) oleo-gum resin(s) and/or one or more (e.g., 1, 2, 3, 4, or more) derivative(s) of an oleo-gum resin. Further exemplary compounds include, but are not limited to, eugenol; m-cresol; cuminaldehyde; α-, β-, and/or γ-commiphoric acids; α- and/or β-heerabomyrrholic acids; pyrocatechin; protocatechuic acid; arabinose; galactose; glucuronic acid; α-pinene; carvone; α-copaene; myrcene; α-thujene; δ-3-carene; p-cymene; β-phellandrene; isolongifolene; α-terpinene; limonene; methoxydecane (e.g., 1-methoxydecane); sabinene; octyl acetate; octanol; bornyl acetate; α-cubebene; α-thujene; γ-terpinene; and any combination thereof.

A particle of the present invention may comprise frankincense or a derivative thereof, myrrh or a derivative thereof, and any combination thereof. In some embodiments, the particle comprises frankincense or a derivative thereof in an amount of about 1%, 5%, 10%, 15%, 20%, 25%, 30%, 35%, 40%, 45%, 50%, 55%, or 60% to about 65%, 70%, 75%, 80%, or 85% by weight of the oleo-gum resin or derivative thereof and/or myrrh or a derivative thereof in an amount of about 1%, 5%, 10%, 15%, 20%, 25%, or 30% to about 35%, 40%, 45%, or 50% by weight of the oleo-gum resin or derivative thereof. In some embodiments, a particle of the present invention comprises frankincense or a derivative thereof in an amount of about 1%, 5%, 10%, 15%, 20%, 25%, 30%, 35%, 40%, 45%, 50%, 55%, 60%, 65%, 70%, 75%, 80%, or 85% by weight of the oleo-gum resin or derivative thereof that is present in and/or on the particle. In some embodiments, a particle of the present invention comprises myrrh or a derivative thereof in an amount of about 1%, 5%, 10%, 15%, 20%, 25%, 30%, 35%, 40%, 45%, or 50% by weight of the oleo-gum resin or derivative thereof that is present in and/or on the particle. In some embodiments, a particle of the present invention comprises frankincense or a derivative thereof and myrrh or a derivative thereof.

The particle may comprise an oleo-gum resin and/or a derivative thereof in an amount of about 1%, 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or more by weight of the particle. In some embodiments, the particle comprises an oleo-gum resin and/or a derivative thereof in an amount of about 1%, 5%, 10%, 15%, 20%, or 25% to about 30%, 35%, 40%, 45%, 50%, 55%, 60%, 65%, 70%, 75%, 80%, 85%, 90%, 95%, 95%, 96%, 97%, 98%, 99%, or more by weight of the particle. In some embodiments, the particle comprises gold in an amount of about 0.0001%, 0.001%, 0.01%, 0.1%, 1%, 5%, 10%, 15%, 20%, or 25% to about 30%, 35%, 40%, 45%, 50%, 55%, 60%, 65%, 70%, 75%, 80%, 85%, 90% or more by weight of the particle. In some embodiments, the particle comprises gold in an amount of about 0.0001%, 0.001%, 0.01%, 0.1%, 1%, 5%, 10%, 15%, 20%, or 25% to about 30%, 35%, 40%, 45%, 50%, 55%, 60%, 65%, 70%, 75%, 80%, 85%, 90% or more by weight of the particle. In some embodiments, the particle comprises gold in an amount of about 0.0001%, 0.001%, 0.01%, 0.1%, or 0.5% to about 1%, 2%, 5%, 10%, 15%, 20%, 25%, 30%, 35%, 40%, 45%, or 50% by weight of the particle, and/or an oleo-gum resin and/or a derivative thereof in an amount of about 50%, 55%, 60%, 65%, or 70% to about 75%, 80%, 85%, 90%, 95%, 96%, 97%, 98%, or 99% by weight of the particle.

A particle of the present invention may further comprise silicon and/or a silicon containing compound such as a silicate, silicic acid, and/or silica. Exemplary silicates include, but are not limited to, sodium silicates, potassium silicates, and/or aluminum silicates (e.g., zeolites). Exemplary silicic acids include, but are not limited to, $H_2SiO_3$, ortho silicic acid ($H_4SiO_4$), colloidal silicic acid (e.g., hydrated silica gel), choline- and/or chloride-stabilized orthosilicic acid, and/or polymers of silicic acids such as di-silicic ($H_2Si_2O_5$) and/or tri-silicic ($H_2Si_3O_7$) acids, and/or hydrates of silicic acids such as pentahydro-silicic ($H_{10}Si_2O_9$) and/or pyro-silicic acid ($H_6Si_2O_7$). In some embodiments, the silica may be colloidal silica and/or silica gel (i.e., amorphous silicon dioxide). Silicon and/or a silicon containing compound may be present in and/or on the particle and may be covalently and/or noncovalently bound to the particle (e.g., to gold and/or to the oleo-gum resin and/or derivative thereof). In some embodiments, a particle of the present invention may comprise silicon and/or a silicon containing compound in an amount of about 5%, 4%, 3%, 2%, 1%, 0.75%, 0.5%, 0.25%, or 0.1% or less by weight of the particle.

A composition of the present invention comprises a particle of the present invention and a carrier. In some embodiments, the carrier comprises water and/or the composition is an aqueous composition. In some embodiments, the carrier is a pharmaceutically acceptable carrier. In some embodiments, the carrier is a base or vehicle of an ointment, cream, gel (e.g., hydrogel), or lotion. A composition of the present invention may be a liquid, solid, or gel. In some embodiments, a composition of the present invention has a pH of about 2, 2.5, 3, 3.5, 4, 4.5, 5, 5.5, or 6 to about 6.5, 7, 7.5, 8, 8.5, 9, 9.5, or 10. In some embodiments, a composition of the present invention has a pH of about 2, 2.5, 3, 3.5, 4, 4.5, 5, 5.5, 6, 6.5, 7, 7.5, 8, 8.5, 9, 9.5, or 10. A particle of the present invention may be suspended in the carrier and/or a composition of the present invention may be a suspension. In some embodiments, the composition is a colloidal suspension. In some embodiments, the composition is a colloidal dispersion. In some embodiments, a particle of the present invention is dissolved in a carrier and/or a composition of the present invention is a solution. In some embodiments, a composition of the present invention is precipitate free. In some embodiments, a composition of the present invention comprises a precipitate and the precipitate may optionally be present in the composition in an amount of about 1 gram or less (e.g., about 0.9, 0.8, 0.7, 0.6, 0.5, 0.4, 0.3, 0.2, 0.1, or less grams) per 10 mL of the composition.

A composition of the present invention may comprise gold in an amount of about 1, 5, 10, 15, 20, 25, 30, 35, 40, 45, 50, 55, 60, 65, 70, or 75 µg of gold per mL of the composition to about 80, 85, 90, 95, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500 µg of gold per mL of the composition, or more. In some embodiments, a composition of the present invention comprises gold in an amount of about 1, 5, 10, 15, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500 µg of gold per mL of composition, or more.

In some embodiments, a particle and/or composition of the present invention may be red, blue, violet, and/or purple in color. In some embodiments, a particle and/or composition of the present invention may absorb light having a wavelength of and/or have a peak surface plasmon resonance (SPR) wavelength of about 300, 350, 400, 450, or 500 nm to about 550, 600, 650, 700, or 750 nm. In some embodiments, a particle and/or composition of the present invention may absorb light having a wavelength of and/or have a peak SPR wavelength of about 300, 350, 400, 450, 500, 550, 600, 650, 700, or 750 nm. A particle and/or composition of the present invention may transmit about 1%, 5%, 10%, 20%, 30%, 40%, 50%, 60%, 70%, 80%, 90%, or more of incident light. In some embodiments, a particle and/or composition of the present invention is purple (e.g., deep reddish purple) in color and/or may transmit about 50% or less (e.g., about 40%, 30%, 20%, 10%, 5%, 1% or less) of incident light.

A composition of the present invention may be stable for at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more days, months, and/or years when stored under recommended storage conditions (e.g., in a closed container stored at room temperature). Stability of the composition may be determined by comparing a property of the composition at an initial time point (e.g., at the time of formation and/or packaging) compared to the same property of the composition at a time point after the initial time point. In some embodiments, stability of the composition is measured by the color of the composition (optionally by visual inspection), amount of light transmitted through the composition, plasmon wavelength, viscosity of the composition, and/or amount of precipitate present in the composition (optionally as determined by visual inspection), optionally with each compared to the respective property at an initial time point. In some embodiments, a composition of the present invention has a color that remains substantially the same shade (e.g., purple) for at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more days, months, and/or years when stored under recommended storage conditions. In some embodiments, the amount of precipitate present in a composition of the present invention does not vary by more than 10% for at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more days, months, and/or years when stored under recommended storage conditions. In some embodiments, the plasmon wavelength of a composition of the present invention upon initial formation (i.e., initial time point) varies by about 10 nm or less (e.g., 9, 8, 7, 6, 5, 4, 3, 2, or 1 nm or less) compared to the plasmon wavelength of the composition when measured at 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more days, months, and/or years after the initial time point, when stored under recommended storage conditions. In some embodiments, the amount of light transmitted by a composition of the present invention does not vary by more than 10% for at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more days, months, and/or years when stored under recommended storage conditions. In some embodiments, the viscosity of a composition of the present invention does not vary by more than 10% for at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more days, months, and/or years when stored under recommended storage conditions.

A composition of the present invention may have a viscosity in a range of about 0.001, 0.005, 0.01, 0.05, 0.1, 0.5, or 1 poise to about 1.5, 2, 2.5, 3, 3.5, 4, 4.5, 5, 5.5, 6, 6.5, 7, 7.5, 8, 8.5, 9, 9.5, or 10 poise, optionally at about 20° C. to about 25° C. and about 1 atm and/or at room temperature and pressure. In some embodiments, a composition of the present invention may have a viscosity of about 0.001, 0.005, 0.01, 0.01, 0.05, 0.1, 0.5, 1, 1.5, 2, 2.5, 3, 3.5, 4, 4.5, 5, 5.5, 6, 6.5, 7, 7.5, 8, 8.5, 9, 9.5, or 10 poise, optionally at about 20° C. to about 25° C. and about 1 atm and/or at room temperature and pressure. In some embodiments, a composition of the present invention has a viscosity similar to the viscosity of water at the same temperature and pressure. For example, the viscosity of a composition of the present invention may be about ±20% or less (e.g., ±15%, 10%, 5%, or less) of the viscosity of water at the same temperature and pressure (e.g., at about 20° C. to about 25° C. and about 1 atm and/or at room temperature and pressure). In some embodiments, a composition of the present invention may have a density in a range of about 0.9, 0.95, 0.96, 0.97, 0.98, 0.99 g/cm$^3$ to about 1, 1.05, 1.1, 1.2, 1.3, 1.4, 1.5 g/cm$^3$ or more, optionally at about 20° C. to about 25° C. and about 1 atm and/or at room temperature and pressure. The density of the composition may be greater than the density of water such as about 5% or more (e.g., 10%, 15%, 20%, 25%, 30% or more) compared to the density of water at the same temperature and pressure (e.g., at about 20° C. to about 25° C. and about 1 atm and/or at room temperature and pressure).

A plurality of particles and/or a composition of the present invention may form a film. In some embodiments, a composition of the present invention may be dried and/or a carrier present in the composition may be removed (e.g., evaporated) to thereby provide a film. A film of the present invention may have a thickness of about 0.5 microns to about 1, 1.5, or 2 microns or more. The thickness of the film may vary by about 20% or less (e.g., by about 10%, 5%, or less). In some embodiments, a film of the present invention has a thickness that varies by about 10 nm or less across the length of the film. A film of the present invention may comprise a plurality of particles (e.g., nanotubes, nanorods, nanofibers) of the present invention and the particles may optionally have a diameter and/or width of about 20, 21, 22, 23, 24, 25, 26, 27, 28, 29, 30, 31, 32, 33, 34, 35, 36, 37, 38, 39, or 40 nm to about 41, 42, 43, 44, 45, 46, 47, 48, 49, 50, 51, 52, 53, 54, or 55 nm.

In some embodiments, a particle and/or composition of the present invention may comprise an active ingredient. An active ingredient may provide the particle and/or composition with an additional property and/or effect (e.g., therapeutic effect). In some embodiments, an active ingredient may be present in and/or on a particle of the present invention (e.g., covalently or noncovalently bound to the particle) and/or may be unbound to a particle of the present invention (e.g., free in solution) in a composition of the present invention. In some embodiments, an active ingredient is dissolved in a composition of the present invention. Exemplary active ingredients include, but are not limited to, botanicals, herbs, supplements, vitamins, minerals, amino acids, nucleic acids, modified nucleic acids, flavoring agents, coloring agents, nutraceuticals, immunogens (e.g., antigens used in a vaccine) and/or therapeutic agents. In some embodiments, a composition of the present invention is administered (e.g., concurrently or simultaneously) with a vaccine or a composition of the present invention is a vaccine (e.g., comprises a particle of the present invention and an immunogen). In some embodiments, a particle and/or composition of the present invention may increase the bioavailability and/or effectiveness of an active ingredient. In some embodiments, a particle and/or composition of the present invention may increase absorption of an active ingredient in the blood stream and/or through cell walls of a subject (e.g., a human, plant, etc.). In some embodiments, an active ingredient improves the flavor and/or color of the particle and/or composition. A particle and/or composition of the present invention may comprise one or more (e.g., 1, 2, 3, 4, 5, or more) different active ingredients. The active ingredient may be present in an amount of about 0.01%, 0.1%, 0.5%, 1%, 5%, 10%, 15%, 20%, or 25% to about 30%, 35%, 40%, 45%, 50%, 55%, 60%, 65%, 70%, 75%, 80%, 85%, 90%, or 95%, or more by weight of the particle and/or composition. In some embodiments, the active ingredient may be present in an amount of about 0.01%, 0.1%, 0.5%, 1%, 5%, or 10% to about 15%, 20%, 25%, 30%, 35%, 40%, 45%, 50%, 55%, 60% , 65%, 70%, or 75% by weight of the particle and/or composition. In some embodiments, the active ingredient may be present in an amount of about 0.01%, 0.1%, 0.5%, 1%, 5%, 10%, 15%, 20%, 25%, 30%, 35%, 40%, 45%, 50%, 55%, 60%, 65%, 70%, 75%, 80%, 85%, 90%, or 95%, or more by weight of the particle and/or composition.

Exemplary active ingredients include, but are not limited to, cinnamon (e.g., *Cinnamomum aromaticum, Cinnamomum camphora,* and/or *Cinnamomum verum*), oregano, garlic, *Camellia sinensis* extracts, steroids, caffeine, cannabidiol (e.g., cannabidiol oil), zinc or a zinc containing compound (e.g., zinc picolinate, zinc oxide, etc.), fenugreek (e.g., fenugreek leaves, seeds, oil, etc.), St. John's wort (*Hypericum perforatum*), S-adenosyl methionine (SAMe), lavender (e.g., lavender oil), chamomile, saffron, docosahexaenoic acid (DHA), gamma aminobutyric acid (GABA), pregnenolone, ribonucleic acids (including natural and/or artificial), deoxyribonucleic acids (including natural and/or artificial), peptide nucleic acids, morpholino- and locked nucleic acids, glycol nucleic acids, threose nucleic acids, 4-hydroxyphenylalanine, resveratrol, icariin, *Panax ginseng,* maca, maca root, yohimbine, *Ginkgo biloba,* omega-3, fish oils, docosahexaenoic acid, curcumin, turmeric, ginseng, 5-hydroxytryptophan (5-HTP), dopamine, levodopa,

*Mucuna* extract, DOPA *Mucuna, Ginkgo biloba*, tyrosine, coenzyme Q10 (CoQ10), *Echinacea*, goldenseal, nucleic acids (including natural and/or artificial), nucleic acid analogues, B vitamins (e.g., vitamin B-1 (thiamine), vitamin B-2 (riboflavin), vitamin B-3 (niacin, nicotinamide, nicotinamide riboside), vitamin B-5 (pantothenic acid), vitamin B-6 (pyridoxine, pyridoxal, pyridoxamine), vitamin B-7 (biotin), vitamin B-9 (folate), and/or vitamin B-12), cobalamins (e.g., cyanocobalamin and/or methylcobalamin), pregnenolone sulfate, DHEA, DHEA sulfate, progesterone, neurosteroids, pregnenolone, pregn-5-en-3β-ol-20-one, P5, 5-pregnenol one, δ5 -pregnene-3β-ol-20-one, NSC-1616, calcium fructate, D-aspartic acid, *Eurycoma longifolia*, tribulin, fenusterols, forslean, suma root, pomegranate extracts, saw palmetto, nettle root, red clover, vitamin c, soy (e.g., miso and/or soy milk), lycopene, fruit extracts (e.g., from guava, watermelon, and/or pink grapefruit), ginger, rosemary, skullcap, basil, holy basil, green tea (EGCG), copper, D Vitamins (e.g., vitamin D, vitamin D1, vitamin D2, vitamin D3, vitamin D4, and/or vitamin D5), fish/animal oil, probiotics, curcumin, biotin, digestive enzymes, ashwagandha, iron, magnesium, chromium, alpha-tocopherol (vitamin e), glucosamine, chondroitin, tyrosine, all-heal (*Valeriana officinalis*), all-heal (*Viscum album*), immortelle (*Helichrysum arenarium*), ginseng (e.g., American ginseng, blue ginseng, Chinese ginseng, ginseng (*Panax ginseng*), oriental ginseng, *Panax ginseng*, red ginseng, siberian ginseng (*Eleutherococcus senticosus*), yellow ginseng, and/or Korean ginseng), capsaicin, chili pepper extracts, black pepper (e.g., *Piper nigrum*), maritime pine bark (pycnogenol), and/or one or more herb(s), botanical(s), vitamin(s), mineral(s), and/or amino acid(s)as described in U.S. Application Ser. No. 62/901,550, which is incorporated herein by reference in its entirety.

In some embodiments, a particle and/or composition of the present invention are in the form of a liquid, gel, cream, ointment, or solid. In some embodiments, a composition of the present invention may be a pharmaceutical composition. In some embodiments, a pharmaceutical composition of the present invention may comprise a particle of the present invention and a pharmaceutically acceptable carrier. Any suitable pharmaceutically acceptable carrier known to those of skill in the art may be used in a pharmaceutical composition of the present invention. "Pharmaceutically acceptable carrier" as used herein refers to a carrier that is compatible with other ingredients in the pharmaceutical composition and that is not harmful or deleterious to the subject, i.e., the carrier can be administered to a subject without causing any undesirable biological effects such as toxicity. A carrier may be a solid or a liquid, or both, and may be formulated with a composition of this invention as a unit-dose formulation, which may contain a particle of the present invention in an amount of about 0.01%, 0.5%, 0.1%, 1%, 5%, 10%, 25%, or 50% to about 60%, 70%, 80%, 90%, 95% or 99% by weight of the composition. In some embodiments, the carrier is water.

A particle of the present invention may be administered to a subject. In some embodiments, a particle of the present invention may be formulated for administration and/or delivery in a carrier in accordance with known techniques. See, e.g., Remington, *The Science and Practice of Pharmacy* (9$^{th}$ Ed. 1995). In some embodiments, a particle of the present invention may be combined (e.g., mixed) with a carrier to form a composition of the present invention. One or more particles may be included in a composition of the present invention.

In some embodiments, a composition of the present invention is suitable for oral, rectal, topical (i.e., both skin and mucosal surfaces, including airway surfaces), buccal (e.g., sub-lingual), vaginal, parenteral (e.g., subcutaneous, intramuscular including skeletal muscle, cardiac muscle, diaphragm muscle and smooth muscle, intradermal, intravenous, and/or intraperitoneal), intranasal, transdermal, intraarticular, intrathecal, and/or inhalation administration, administration to the liver by intraportal delivery, and/or direct organ injection (e.g., into the liver, into the brain for delivery to the central nervous system, into the pancreas, or into a tumor or the tissue surrounding a tumor). The most suitable route in any given case will depend on the nature and severity of the disease, disorder, or condition being treated and on the nature of the particular particle that is being used. In some embodiments, a particle and/or composition of the present invention is suitable for oral and/or topical administration.

In some embodiments, a particle and/or composition of the present invention may be suitable for intrathecal delivery and/or may be administered to a subject in need thereof intrathecally. In some embodiments, a particle and/or composition of the present invention may be administered by intrathecal injection and/or by a pump providing intrathecal delivery.

For injection, the carrier may be a liquid, such as sterile pyrogen-free water, pyrogen-free phosphate-buffered saline solution, bacteriostatic water, or CREMOPHOR® EL[R] (BASF, Parsippany, N.J.). For other methods of administration, the carrier may be a solid or liquid.

For oral administration, the particle and/or composition may be administered in solid dosage forms, such as capsules, tablets, and powders, or in liquid dosage forms, such as elixirs, syrups, and suspensions. Particles may be encapsulated in gelatin capsules together with inactive ingredients and/or powdered carriers, such as glucose, lactose, sucrose, mannitol, starch, cellulose, cellulose derivatives, magnesium stearate, stearic acid, sodium saccharin, talcum, magnesium carbonate and/or the like. Examples of additional inactive ingredients that may be added to provide desirable color, taste, stability, buffering capacity, dispersion or other known desirable features are red iron oxide, silica gel, sodium lauryl sulfate, titanium dioxide, edible white ink and/or the like. Similar diluents may be used to make compressed tablets. Both tablets and capsules may be manufactured as sustained release products to provide for continuous release of particles and/or an active ingredient over a period of hours. Compressed tablets may be sugar coated or film coated to mask any unpleasant taste and protect the tablet from the atmosphere, or enteric- coated for selective disintegration in the gastrointestinal tract. Liquid dosage forms for oral administration may contain coloring and/or flavoring to increase subject acceptance. In some embodiments, a composition of the present invention is a liquid (e.g., a suspension of particles in a carrier such as water).

Formulations suitable for buccal (sub-lingual) administration include lozenges comprising the particle in a flavored base such as sucrose, *Acacia*, and/or tragacanth; and pastilles comprising the particle in an inert base such as gelatin, glycerin, sucrose, and/or *Acacia*.

Formulations suitable for parenteral administration include sterile aqueous and non-aqueous injection solutions comprising the particle, which preparations are preferably isotonic with the blood of the intended recipient. These preparations may contain anti-oxidants, buffers, bacteriostats, and/or solutes which render the formulation isotonic with the blood of the intended subject. Aqueous and non-aqueous sterile suspensions may include suspending agents and thickening agents. The formulations may be presented in unit\dose or multi-dose containers, for example sealed ampoules and vials, and may be stored in a freeze-dried (lyophilized) condition requiring only the addition of the sterile liquid carrier, for example, saline or water-for-injection immediately prior to use.

Extemporaneous injection solutions and suspensions may be prepared from sterile powders, granules and tablets of the kind previously described. For example, in some embodiments, there is provided an injectable, stable, sterile composition comprising a particle of the invention, in a unit dosage form in a sealed container. The particle may be provided in the form of a lyophilizate which is capable of being reconstituted with a suitable pharmaceutically acceptable carrier to form a liquid composition suitable for injection thereof into a subject. The unit dosage form typically comprises from about 10, 20, 30, 40, or 50 micrograms to about 60, 70, 80, 90, 100, 150, or 200 micrograms of gold. An emulsifying agent that is pharmaceutically acceptable may be employed in sufficient quantity to emulsify the particle in an aqueous carrier. One such useful emulsifying agent is phosphatidyl choline.

Formulations suitable for rectal administration may be presented as unit dose suppositories. These may be prepared by admixing the particles with one or more conventional solid carriers, for example, cocoa butter, and then shaping the resulting mixture.

In some embodiments, formulations suitable for topical application to the skin are in the form of an ointment, cream, liquid, lotion, paste, gel, spray, aerosol, or oil. Carriers which may be used include water, petroleum jelly, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, Tyle, *Pharm. Res.* 3:318 (1986), which is incorporated by reference herein in its entirety) and typically take the form of an optionally buffered aqueous solution including the particle. Suitable formulations comprise citrate or bis/tris buffer (pH 6) or ethanol/water and contain from 0.1 to 0.2M of the particle.

The particle may alternatively be formulated for nasal administration or otherwise administered to the lungs of a subject by any suitable means, e.g., administered by an aerosol suspension of respirable particles comprising a particle of the present invention, which the subject inhales. The respirable particles may be liquid or solid. The term "aerosol" includes any gas-borne suspended phase, which is capable of being inhaled into the bronchioles or nasal passages. Specifically, aerosol includes a gas-borne suspension of droplets, as may be produced in a metered dose inhaler or nebulizer, or in a mist sprayer. Aerosol also includes a dry powder composition suspended in air or other carrier gas, which may be delivered by insufflation from an inhaler device, for example. See Ganderton & Jones, *Drug Delivery to the Respiratory Tract,* Ellis Horwood (1987); Gonda (1990) *Critical Reviews in Therapeutic Drug Carrier Systems* 6:273-313; and Raeburn et al., *J. Pharmacol. Toxicol. Meth.* 27:143 (1992). Aerosols of liquid particles comprising a particle of the present invention may be produced by any suitable means, such as with a pressure-driven aerosol nebulizer or an ultrasonic nebulizer, as is known to those of skill in the art. See, e.g., U.S. Pat. No. 4,501,729.

Aerosols of solid particles comprising a particle of the present invention may likewise be produced with any solid particulate medicament aerosol generator, by techniques known in the pharmaceutical art.

In some embodiments, a particle and/or composition of the present invention may be administered in a local rather than systemic manner, for example, by injection, in a depot or sustained-release formulation.

In some embodiments, a composition of the present invention may comprise a pH-adjusting agent (e.g., an acid such as hydrochloric acid, a base or buffer such as sodium lactate, sodium acetate, sodium phosphate, sodium citrate, sodium borate, or sodium gluconate). In some embodiments, a composition of the present invention may comprise a preservative such as a methylparaben, propylparaben, and/or benzyl alcohol. In some embodiments, a composition of the present invention is devoid of additives or agents (e.g., pH-adjusting agents, preservatives, etc.) other than an active ingredient and/or those used to form the particle and/or those provided in forming the particle.

According to some embodiments, a method of making a particle of the present invention is provided. The method comprises combining an oleo-gum resin and/or a derivative thereof and a solution comprising soluble gold to form a mixture and forming the particle from the mixture, wherein the particle comprises gold and the oleo-gum resin and/or a derivative thereof. In some embodiments, an oleo-gum resin is combined with soluble gold. The oleo-gum resin may be in solid form (e.g., powder, tear, etc.) and/or is a raw oleo-gum resin (e.g., dried exudate in the form of a powder or tear). In some embodiments, the oleo-gum resin and/or a derivative of the oleo-gum resin dissolves in water and/or the mixture. In some embodiments, the oleo-gum resin and/or a derivative of the oleo-gum resin is insoluble in water and/or the mixture. The oleo-gum resin and/or a derivative of the oleo-gum resin may be suspended or dispersed in the water and/or mixture. An oleo-gum resin and/or a derivative thereof may function to reduce gold to thereby form and/or provide a particle comprising gold (e.g., a gold nanoparticle) and/or an oleo-gum resin and/or a derivative thereof may function to stabilize the particle, optionally in water.

In some embodiments, other than an oleo-gum resin and/or a derivative thereof, a method of the present invention and/or the mixture from which a particle is formed may be devoid of a reducing agent and/or a stabilizing agent. That is, other than an oleo-gum resin and/or a derivative thereof, a method and/or mixture of the present invention may be devoid of an added agent that functions as a reducing agent (e.g., citrate ions) and/or a stabilizing agent to form and/or stabilize a particle of the present invention such as a reducing agent and/or stabilizing agent known in the art to reduce and/or stabilize soluble gold and/or gold particles (e.g., gold nanoparticles). In some embodiments, a composition, mixture, and/or particle of the present invention is substantially free of a traditional reducing agent (i.e., an agent known in the art to reduce gold to form a gold nanoparticle) such as citrate (e.g., citrate ions), citric acid, a borohydride (e.g., sodium borohydride), polyethyleneimine, ascorbate, and/or ascorbic acid in that the traditional reducing agent is not present in an amount sufficient to form and/or stabilize a particle of the present invention. A method of the present invention may not comprise a step of reducing soluble gold with a traditional reducing agent and/or capping or stabilizing a gold particle using a traditional reducing agent. In some embodiments, a composition, mixture, and/or particle of the present invention is devoid of citrate (e.g., citrate ions), citric acid, a borohydride (e.g., sodium borohydride), polyethyleneimine, ascorbate, and/or ascorbic acid. A particle of the present invention may not be prepared in accordance with the Turkevich and/or Frenz method for gold nanoparticle synthesis, which prepares gold nanoparticles by reduction using citrate (e.g., sodium citrate such as trisodium citrate or trisodium citrate dihydrate). In some embodiments, a method of the present invention does not involve a step of reducing soluble gold using citrate (e.g., sodium citrate such as trisodium citrate) and/or ascorbic acid and/or does not involve capping gold particles using citrate (e.g., sodium citrate such as trisodium citrate) and/or ascorbic acid. A surface of a particle of the present invention may be devoid of citrate and/or a citrate ion. In some embodiments, an oleo-gum resin and/or a derivative thereof directly contacts the surface of a particle of the present invention in that there is no intermediate material (e.g., a reducing agent or capping agent such as a citrate ion) between the surface of the particle and the oleo-gum resin and/or a derivative thereof. In some embodiments, a particle of the present invention is not a citrate-reduced particle, an ascorbic acid-reduced particle, a polyethyleneimine-reduced particle, or a borohydride-reduced particle.

In some embodiments, an oleo-gum resin (e.g., raw oleo-gum resin) is combined with water prior to being combined with the solution comprising soluble gold. In some embodiments, water is heated (e.g., to a temperature in a range of about 40° C. to about 150° C., optionally to boiling) to form heated water (e.g., boiling water), and an oleo-gum resin or a derivative thereof is added to the heated water. The soluble gold may then be added to the heated water comprising the oleo-gum resin or derivative thereof. In some embodiments, a derivative of the oleo-gum resin may form in the water and/or upon combination and/or reaction with soluble gold.

Upon adding an oleo-gum resin (e.g., in the form of a powder and/or tear) to water, the water with the oleo-gum resin may have a viscosity of about 1000 poise or more such as about 1,000, 5,000, or 10,000 poise to about 25,000, 50,000, 100,000, 150,000, 200,000, 250,000 poise or more. Upon combining a solution comprising soluble gold and an oleo-gum resin (e.g., in the form of a powder and/or tear) to form a mixture, the mixture may have a viscosity that decreases over time and/or as particles form (e.g., as the number of particles in the mixture increases) and/or the mixture may have a density that increases over time and/or as particles form (e.g., as the number of particles in the mixture increases). The mixture, optionally including particles (e.g., gold nanoparticles), may have a viscosity in a range of about 0.001, 0.005, 0.01, 0.05, 0.1, 0.5, or 1 poise to about 1.5, 2, 2.5, 3, 3.5, 4, 4.5, 5, 5.5, 6, 6.5, 7, 7.5, 8, 8.5, 9, 9.5, or 10 poise, optionally at about 20° C. to about 25° C. and about 1 atm and/or at room temperature and pressure. While not wishing to be bound to any particular theory, the soluble gold and/or particles may make an oleo-gum resin and/or a derivative thereof soluble, optionally due to a chelating effect. In some embodiments, the mixture, optionally including particles (e.g., gold nanoparticles), may have a density in a range of about 0.9, 0.95, 0.96, 0.97, 0.98, 0.99 g/cm$^3$ to about 1, 1.05, 1.1, 1.2, 1.3, 1.4, 1.5 g/cm$^3$ or more, optionally at about 20° C. to about 25° C. and about 1 atm and/or at room temperature and pressure. The density of the mixture may be greater than the density of water such as about 5% or more (e.g., 10%, 15%, 20%, 25%, 30% or more) than the density of water at the same temperature and pressure (e.g., at about 20° C. to about 25° C. and about 1 atm and/or at room temperature and pressure). In some embodiments, the density of the mixture increases from less than about 0.998 g/cm$^3$ to greater than about 1 g/cm$^3$ or 1.01 g/cm$^3$, optionally over a period of time such as from upon initial combination of the solution comprising soluble gold and an oleo-gum resin to a time during and/or after formation of particles.

Soluble gold may include gold II) and/or gold (III) and/or be an acid and/or salt of gold. In some embodiments, the soluble gold is chloroauric acid and/or auric chloride. In some embodiments, soluble gold (e.g., chloroauric acid) may be provided by acidifying an aqueous composition comprising a gold salt such as, but not limited to, sodium tetrachloroaurate (NaAuCl$_4$), potassium tetrachloroaurate (KAuCl4), and/or magnesium tetrachloroaurate (Mg(AuCl$_4$)$_2$). In some embodiments, a gold salt in water may be acidified with an acid (e.g., HCl) in a molar ratio in a range of about 2:1 to about 1:2 (gold salt:acid), optionally in a 1:1 molar ratio (gold salt:acid). In some embodiments, soluble gold (e.g., chloroauric acid) may be provided by dissolving solid gold using aqua regia (i.e., a mixture of nitric acid and hydrochloric acid). For example, solid metallic gold may be dissolved in a solution comprises nitric acid and hydrochloric acid in a molar ratio of about 4:1, 3:1, 2:1, or 1:1 to about 2:1, 3:1, or 4:1.

An oleo-gum resin or a derivative thereof and soluble gold may be combined in a weight ratio of about 2000:1, 1000:1, 500:1, or 200:1 to about 100:1, 50:1, or 1:1 (oleo-gum resin or derivative thereof:soluble gold). In some embodiments, more oleo-gum resin or a derivative thereof by weight is combined with soluble gold by weight, optionally such that, in some embodiments, the gold (e.g., soluble gold) is super saturated with the oleo-gum resin and/or derivative thereof. In some embodiments, the oleo-gum resin and/or derivative thereof is combined with soluble gold in an amount such that there is excess oleo-gum resin and/or derivative thereof in the composition.

In some embodiments, the combining step comprises heating water to a temperature in a range of about 40° C. to about 150° C. to form heated water (e.g., boiling water), and adding the oleo-gum resin or derivative thereof and/or soluble gold to the heated water to form the mixture. In some embodiments, the combining step comprises heating water to a temperature in a range of about 40° C. to about 150° C. to form heated water (e.g., boiling water) and adding an oleo-gum resin (e.g., powdered and/or teared) to the heated water to form a heated oleo-gum resin composition. The heated oleo-gum resin composition may be brought to a temperature in a range of about 40° C. to about 150° C. and/or may be boiling. In some embodiments, the heated oleo-gum resin composition may be a thick tar-like composition and/or the solid oleo-gum resin (e.g., powdered and/or teared) may no longer be visible. In some embodiments, the heated oleo-gum resin composition may be heated until solid oleo-gum resin (e.g., powdered and/or teared) is no longer visible. Soluble gold may be added to the heated oleo-gum resin composition to form the mixture. Upon adding soluble gold to an oleo-gum resin and/or a derivative thereof (e.g., an aqueous composition comprising the oleo-gum resin and/or derivative thereof or a heated oleo-gum resin composition), the composition may change in appearance such as change from a yellow and/or brown color to a purplish color and/or the viscosity of the composition may decrease. In some embodiments, the solution comprising soluble gold and/or the mixture including soluble gold and the oleo-gum resin and/or derivative thereof are heated to a temperature in a range of about 40° C. to about 150° C., optionally to boiling, for a time period of about 1 minute to about 5, 10, 15, 20, 30, 40, 50, or 60 minutes. In some embodiments, the mixture is not heated upon combining the solution comprising soluble gold and/or the oleo-gum resin and/or derivative thereof and/or the mixture is allowed to cool to room temperature. In some embodiments, a method of the present invention forms a particle of the present invention at room temperature and/or at a temperature in a range of about 20° C., 30° C., 40° C., 50° C., or 60° C. to about 70° C., 80° C., 90° C., 100° C., 110° C., 120° C., 130° C., 140° C., or 150° C.

After forming the particles, the mixture including particles of the present invention may also comprise insoluble material and/or a precipitate. In some embodiments, a composition of the present invention (e.g., a pharmaceutical composition) is the mixture including particles of the present invention and optionally insoluble material and/or a precipitate. In some embodiments, upon forming the particles, the mixture may be filtered. Filtering may be performed using methods known in the art such as, but not limited to, passing the mixture, optionally with the use of suction, through glass wool, a cheese cloth, a paper filter, a particulate filter (e.g., diatomaceous earth), and/or a porous metal frit. Filtering may remove a portion (e.g., at least about 5%, 25%, 50%, 75%, or 90%) or all of the insoluble material and/or precipitate. The filtrate (i.e., liquid passed through a filter) may comprise a particle of the present invention. In some embodiments, a composition of the present invention comprises and/or is the filtrate. In some embodiments, the filtrate is used to prepare a composition of the present invention (e.g., the filtrate is diluted, optionally with water, to provide the composition). In some embodiments, the solid that did not pass through the filter (i.e., the filter cake) comprises a particle of the present invention. In some embodiments, the filter cake is a composition of the present invention and/or is used to prepare a composition of the present invention (e.g., combined with a lotion, cream, oil, etc.). In some embodiments, silicon and/or a silicon containing compound is added to a particle and/or composition of the present invention via a filtering step. For example, a particle and/or composition of the present invention may be filtered through diatomaceous earth and/or a zeolite and thereby silicon and/or a silicon containing compound may bound to the particle (e.g., covalently and/or noncovalently) and/or may be added to the composition.

In some embodiments, an active ingredient is added to a soluble gold solution, an oleo-gum resin and/or a derivative thereof, and/or a mixture comprising soluble gold and an oleo-gum resin and/or a derivative thereof. An active ingredient may be added prior to formation of a particle of the present invention. In some embodiments, an active ingredient is added to a soluble gold solution and/or combined with an oleo-gum resin and/or a derivative thereof (e.g., a composition comprising an oleo-gum resin and/or a derivative thereof) such that the active ingredient is combined along with the soluble gold and oleo-gum resin and/or derivative thereof to form a mixture that is used to form a particle of the present invention. In some embodiments, an active ingredient is added during and/or after formation of a particle of the present invention (e.g., to the mixture including particles of the present invention). One or more (e.g., 1, 2, 3, 4, or more) active ingredient(s) may be added before, during and/or after particle formation and one or more active ingredient(s) may be added at different times. In some embodiments, an active ingredient is added to a composition of the present invention.

In some embodiments, a method of the present invention comprises converting a solid oleo-gum resin and/or a solid active ingredient to a liquid. In some embodiments, a method of the present invention comprises decreasing the viscosity of an oleo-gum resin and/or an active ingredient. The method of converting a solid to a liquid and/or decreasing the viscosity may comprise combining an oleo-gum resin and/or a derivative thereof and a solution comprising soluble gold, optionally including an active ingredient, to form a mixture as described herein; and forming a particle from the mixture as described herein. Converting a solid to a liquid and/or decreasing the viscosity of an oleo-gum resin and/or an active ingredient may provide the oleo-gum resin and/or active ingredient in an enhanced or improved form for use and/or provide an easier, greener, and/or more efficient method of preparation. In some embodiments, converting a solid to a liquid and/or decreasing the viscosity of an oleo-gum resin and/or an active ingredient may provide an enhanced oil (e.g., essential oil).

Provided according to some embodiments are methods of administering to a subject a particle of the present invention and/or a composition of the present invention. In some embodiments, a particle and/or composition of the present invention is administered to a subject as desired and/or as needed by the subject. In some embodiments, a particle and/or composition of the present invention is administered to a subject as a supplement (e.g., a herbal supplement, a dietary supplement, a health supplement, and/or a nutritional supplement), optionally as desired and/or on a regular basis (e.g., once a day or once a week). Thus, in some embodiments, a particle and/or composition may be a supplement (e.g., a herbal supplement, a dietary supplement, a health supplement, and/or a nutritional supplement) and/or may be used and/or administered as a supplement (e.g., a herbal supplement, a dietary supplement, a health supplement, and/or a nutritional supplement). In some embodiments, a method of the present invention comprises treating and/or preventing a disease, disorder, or condition in a subject (optionally a subject in need thereof), the method comprising administering to the subject a particle of the present invention and/or a composition of the present invention, thereby treating and/or preventing the disease, disorder, or condition in a subject. In some embodiments, the subject is administered the particle and/or composition after fasting for at least about 4, 6, 8, 10, 12, 14, 16, 18, 20, 22, 24, 26, 28, 30, 32, 34, 36, or 38 hours.

In some embodiments, a method of the present invention comprises administering a therapeutically effective amount of a particle and/or composition of the present invention to a subject. As used herein, the term "therapeutically effective amount" refers to an amount of a particle and/or composition of the present invention that elicits a therapeutically useful response in a subject. Those skilled in the art will appreciate that the therapeutic effects need not be complete or curative, as long as some benefit is provided to the subject.

"Treat," "treating" or "treatment of" (and grammatical variations thereof) as used herein refer to any type of treatment that imparts a benefit to a subject and may mean that the severity of the subject's disease, disorder, or condition is reduced, at least partially improved or ameliorated and/or that some alleviation, mitigation or decrease in at least one clinical symptom associated with the disease, disorder, or condition is achieved and/or there is a delay in the progression of the symptom.

In some embodiments, a particle and/or composition of the present may be administered to a subject in a treatment effective amount. A "treatment effective" amount as used herein is an amount that is sufficient to treat (as defined herein) a subject. Those skilled in the art will appreciate that the therapeutic effects need not be complete or curative, as long as some benefit is provided to the subject. In some embodiments, a treatment effective amount may be achieved by administering a composition of the present invention.

The terms "prevent," "preventing" and "prevention" (and grammatical variations thereof) refer to avoidance, reduction and/or delay of the onset of a symptom associated with a disease, disorder, or condition and/or a reduction in the severity of the onset of symptom associated with a disease, disorder, or condition relative to what would occur in the absence of a method of the present invention. The prevention can be complete, e.g., the total absence of the symptom. The prevention can also be partial, such that the occurrence of the symptom in the subject and/or the severity of onset is less than what would occur in the absence of a method of the present invention.

In some embodiments, a particle and/or composition of the present invention may be administered in a prevention effective amount. A "prevention effective" amount as used herein is an amount that is sufficient to prevent (as defined herein) a symptom associated with a disease, disorder, or condition in a subject. Those skilled in the art will appreciate that the level of prevention need not be complete, as long as some benefit is provided to the subject. In some embodiments, a prevention effective amount may be achieved by administering a composition of the present invention.

The present invention finds use in both veterinary, medical, agricultural, and plant applications. In some embodiments, the subject is a plant such as, but not limited to, a plant grown as a crop (e.g., a food crop) and/or a fruit producing plant. In some embodiments, the subject is a fish. In some embodiments, the subject is a mammalian subject. Exemplary mammals of the present invention include, but are not limited to, canines, felines, bovines, caprines, equines, ovines, porcines, rodents (e.g. rats and mice), lagomorphs, primates (e.g., simians and humans), non-human primates (e.g., monkeys, baboons, chimpanzees, gorillas), and the like, and mammals in utero. Mammalian subjects (e.g., human subjects) of both genders and at any stage of development (e.g., neonate, infant, juvenile, adolescent, and/or adult) may be administered a particle and composition of the present invention. In some embodiments, the subject is a human. In some embodiments, the subject is a human adolescent and/or adult.

A method of the present invention may also be carried out on animal subjects, particularly mammalian subjects such as mice, rats, dogs, cats, livestock and horses. In some embodiments, a method of the present invention comprising administering a particle and/or composition of the present invention to an animal subject for veterinary purposes, for drug screening, and/or for drug development purposes.

In some embodiments, the subject is "in need of" or "in need thereof" a method of the present invention, for example, the subject has findings typically associated with a disease, disorder, or condition, is suspected to have a disease, disorder, or condition, and/or the subject has a disease, disorder, or condition.

In some embodiments, a particle and/or composition of the present invention may be administered to a plant and the plant and/or a product thereof (e.g., a fruit thereof) may comprise the particle and/or composition. In some embodiments, the plant that has been administered the particle and/or composition and/or a product of the plant (e.g., a fruit, leaf, flower, etc.) is administered to an animal (e.g., a mammal) or fish to thereby administer the particle and/or composition to the animal or fish.

In some embodiments, an oleo-gum resin and/or a derivative thereof and gold (e.g., a gold particle such as a gold nanoparticle) are compatible with each other such that a particle and/or composition comprising gold and the oleo-gum resin and/or derivative thereof can enhance one or more beneficial effect(s) of the oleo-gum resin and/or derivative thereof and/or gold. In some embodiments, a particle and/or composition comprising gold and an oleo-gum resin and/or a derivative thereof can provide an additive effect (i.e., the effect of the gold and the oleo-gum resin and/or derivative thereof is equal to the sum of the effect of the two ingredients (i.e., gold and the oleo-gum resin and/or derivative thereof) taken separately). In some embodiments, a particle and/or composition comprising gold and an oleo-gum resin and/or a derivative thereof can be synergistic.

"Synergistic", "synergy", and grammatical variants thereof as used herein refer to a particle and/or composition of the present invention exhibiting an effect greater than the effect that would be expected from the sum of the effect of the components of the particle and/or composition individually (e.g., the effect of gold alone and the effect of an oleo-gum resin and/or a derivative thereof alone). For example, in some embodiments, the terms "synergistic" or "synergy" with regard to a particle and/or composition of the present invention that is administered to a subject refers to an effect (e.g., a therapeutic effect such as efficacy for the treatment and/or prevention of a disease, disorder, or condition in the subject) that is greater than that which would be expected from the sum of the individual effects of gold alone (e.g., gold particles such as gold nanoparticles) and the oleo-gum resin and/or derivative thereof alone, optionally via the same mode of administration and/or same concentration. In some embodiments, a particle and/or composition of the present invention provides a synergistic effect for frankincense and/or a derivative thereof and/or for myrrh and/or a derivative thereof in that the sum of the effect for frankincense and/or a derivative thereof alone and/or for myrrh and/or a derivative thereof alone together with the effect of gold alone is less than the effect observed for the particle and/or composition comprising frankincense and/or a derivative thereof and/or for myrrh and/or a derivative thereof. Exemplary benefits and/or effects frankincense and/or a derivative thereof may exhibit include, but are not limited to, anti-inflammatory, antibacterial, antimicrobial, antiseptic, antiviral, analgesic, anti-apoptosis, life-extending, and/or anti-tumor properties/effects upon administration to a subject. Exemplary benefits and/or effects myrrh and/or a derivative thereof may exhibit include, but are not limited to, antibacterial, antimicrobial, antiseptic, antifungal, antioxidant, analgesic, muscle relaxant, reduction in atherogenesis, anti-apoptosis, life-extending, and/or reduction in cholesterol properties/effects upon administration to a subject. In some embodiments, a particle and/or composition of the present invention provides a synergistic effect for an active ingredient in that administration of a particle and/or composition comprising the active ingredient to the subject provides an effect (e.g., a therapeutic effect) that is greater than that which would be expected from the sum of the individual effects of gold alone (e.g., gold particles such as gold nanoparticles), the oleo-gum resin and/or derivative thereof alone, and the active ingredient alone, optionally via the same mode of administration and/or same concentration.

A particle and/or composition of the present invention may provide one or more beneficial effect(s) (e.g., a synergistic effect and/or therapeutic effect) in that the efficacy is enhanced compared to the efficiency of a component alone and/or compared to the sum of the efficacy of the components alone. In some embodiments, the dose to achieve a beneficial effect for one or more of the component(s) of a particle and/or composition of the present invention is reduced compared to the dose required to achieve a beneficial effect for the component alone. In some embodiments, a particle and/or composition of the present invention reduces a side effect associated with a component the particle and/or composition. "Enhanced" as used herein in reference to a property (e.g., an effect) refers to any improvement in producing the desired effect or result. In some embodiments, a particle and/or composition of the present invention may enhance efficacy by increasing efficacy (e.g., increasing the extent or amount of a desired result) compared to the efficacy achieved by at least one of the components of the particle and/or composition alone. As one skilled in the art will recognize, an increase in efficacy may be a decrease or reduction in a clinical symptom associated with a disease, disorder, and/or condition, such as, for example, a decrease in pain and/or a decrease in the size of a lesion. In some embodiments, a particle and/or composition of the present invention provides and/or allows for a lower dose of an active ingredient and/or may provide the same and/or an increased therapeutic and/or prophylactic effect compared to the therapeutic and/or prophylactic effect achieved with the active ingredient alone.

Synergy or a synergistic effect can be calculated using methods known to those of skill in the art. For example, using suitable methods including, but not limited to, the Sigmoid-Emax equation (Holford, N. H. G. and Scheiner, L. B., Clin. Pharmacokinet. 6: 429-453 (1981)), the equation of Loewe additivity (Loewe, S. and Muischnek, H., Arch. Exp. Pathol Pharmacol. 114: 313-326 (1926)) and the median-effect equation (Chou, T. C. and Talalay, P., Adv. Enzyme Regul. 22: 27-55 (1984)). Each equation referred to above can be applied to experimental data to generate a corresponding graph to aid in assessing the effects of the drug combination. The corresponding graphs associated with the equations referred to above are the concentration-effect curve, isobologram curve and combination index curve, respectively.

A particle and/or composition of the present invention may be administered at a dose suitable to achieve a beneficial effect. In some embodiments, a particle and/or composition of the present invention is administered in a therapeutically effective amount. In some embodiments, a particle and/or composition of the present invention is administered to the subject at a dose that achieves an additive effect or a synergistic effect.

A method of the present invention may comprise administering an active ingredient (e.g., a botanical, supplement, vitamin, therapeutic agent) to a subject. In some embodiments, the active ingredient is administered concurrently with a particle and/or composition of the present invention. The particle and/or composition may comprise the active ingredient. In some embodiments, the active ingredient is present in a separate, different composition than the composition of the present invention. The separate, different composition may be administered concurrently with the composition of the present invention and/or may be administered at a different time than the composition of the present invention (e.g., before and/or after administration of the composition of the present invention).

A particle, composition, and/or method of the present invention may increase bioavailability and/or absorption of an oleo-gum resin and/or a derivative thereof in the subject compared to bioavailability and/or absorption of the oleo-gum resin and/or derivative thereof administered to the subject alone. In some embodiments, a particle, composition, and/or method of the present invention may increase bioavailability and/or absorption of frankincense or a derivative thereof in a subject compared to the bioavailability and/or absorption of frankincense or a derivative thereof alone. In some embodiments, a particle, composition, and/or method of the present invention may increase bioavailability and/or absorption of myrrh or a derivative thereof in a subject compared to the bioavailability and/or absorption of myrrh or a derivative thereof alone. In some embodiments, a composition, and/or method of the present invention may increase bioavailability and/or absorption of an active ingredient in the subject compared to bioavailability and/or absorption of the active ingredient administered to the subject alone. For example, a particle, composition, and/or method of the present invention may increase bioavailability and/or absorption of an oleo-gum resin and/or a derivative thereof and/or an active ingredient in the subject by at least about 5%, 10%, 15%, 20%, 25%, 30%, 35%, 40%, 45%, 50%, 55%, 60%, 65%, 70%, 75%, 80%, 85%, 90%, 95%, 100%, 150%, 200%, 300%, 400%, 500% or more compared to bioavailability and/or absorption of the oleo-gum resin and/or derivative thereof and/or the active ingredient administered to the subject alone. In some embodiments, an active ingredient and a particle and/or composition of the present invention are administered to a subject at a dose that achieves an additive effect. In some embodiments, an active ingredient and a particle and/or composition of the present invention are administered to a subject at a dose that achieves a synergistic effect.

A particle, composition, and/or method of the present invention may have and/or provide upon administration to a subject one or more properties and/or effects such as, but not limited to, anti-inflammatory, antibacterial, antimicrobial, antiseptic, antiviral, analgesic, anticancer, anti-tumor, antifungal, antioxidant, analgesic, muscle relaxant, reduction in atherogenesis, reduction in cholesterol, no or minimal adverse side effects, no or minimal cytotoxicity, anti-apoptosis, anti-arthritic, enhanced or increased blood flow, anti-carcinogenic, enhancement of a therapeutic, modification of a disease, and/or life extending properties/effects. In some embodiments, a particle composition, and/or method of the present invention is and/or provides a disease modifying therapeutic such that the particle, composition and/or method modify the disease itself and/or modify a function of the disease. For example, a particle of the present invention may bind (e.g., covalently and/or noncovalently) to and/or interact with a nucleic acid of a microorganism (e.g., virus, bacteria, fungi, etc.), and may modify (e.g., increase or decrease) one or more properties/functions of the microorganism such as reduce its ability to reproduce, reduce its infectivity rate and/or infectivity factor, etc. In some embodiments, a particle, composition and/or method of the present invention has anti-inflammatory properties and/or upon administration to a subject reduces inflammation in the subject, optionally wherein the particle, composition and/or method affects one, two or more inflammation pathways. In some embodiments, a particle, composition and/or method of the present invention may affect two major inflammation pathways: 5-lipoxygenase (5-LOX) and cyclooxygenase-2 (COX-2).

In some embodiments, a particle, composition, and/or method of the present invention may selectively target, treat, and/or kill diseased cells (e.g., virally infected cells, cancer and/or tumor cells, etc.) compared to healthy cells (e.g., non-infected cells and/or noncancerous cells). In some embodiments, a particle, composition, and/or method of the present invention may increase apoptosis in diseased cells contacted with the particle and/or composition and/or in a subject administered the particle and/or composition by at least about 5%, 10%, 15%, 20%, 25%, 30%, 35%, 40%, 45%, 50%, 55%, 60%, 65%, 70%, 75%, 80%, 85%, 90%, 95%, 100%, 150%, 200%, 300%, 400%, 500% or more compared to the amount of apoptosis in diseased cells in the absence of a particle, composition, and/or method of the present invention. In some embodiments, a particle, composition, and/or method of the present invention may decrease apoptosis in healthy cells contacted with the particle and/or composition and/or in a subject administered the particle and/or composition by at least about 5%, 10%, 15%, 20%, 25%, 30%, 35%, 40%, 45%, 50%, 55%, 60%, 65%, 70%, 75%, 80%, 85%, 90%, 95%, or more compared to the amount of apoptosis in healthy cells in the absence of a particle, composition, and/or method of the present invention. In some embodiments, a particle, composition, and/or method of the present invention may increase lifespan, optionally projected lifespan, of a cell contacted with and/or administered the particle and/or composition by at least about 5%, 10%, 15%, 20%, 25%, 30%, 35%, 40%, 45%, 50%, 55%, 60%, 65%, 70%, 75%, 80%, 85%, 90%, 95%, 100%, 150%, 200%, 300%, 400%, 500% or more compared to lifespan of a control cell (e.g., a cell of the same type) in the absence of a particle, composition, and/or method of the present invention. In some embodiments, a particle, composition, and/or method of the present invention may increase lifespan, optionally projected lifespan, of a subject administered the particle and/or composition by at least about 5%, 10%, 15%, 20%, 25%, 30%, 35%, 40%, 45%, 50%, 55%, 60%, 65%, 70%, 75%, 80%, 85%, 90%, 95%, 100%, 150%, 200%, 300%, 400%, 500% or more compared to lifespan of the subject (or of one or more control (e.g., similar) subject(s)), optionally projected lifespan, in the absence of a particle, composition, and/or method of the present invention.

A particle, composition and/or method of the present invention may selectively target dangerous and/or toxic pathogens. For example, a particle, composition and/or method of the present invention may have increased toxicity to disease causing pathogens such as viruses and/or may increase apoptosis of cells infected with disease causing pathogens such as viruses. In some embodiments, a particle, composition and/or method of the present invention may selectively target cancer cells over healthy cells. For example, a particle, composition and/or method of the present invention may increase apoptosis of cancer cells compared to healthy cells. In some embodiments, a particle, composition and/or method of the present invention may protect healthy cells from infection (e.g., from a viral infection) and/or disease.

According to some embodiments, a particle, composition and/or method of the present invention may treat and/or prevent a viral disease and/or infection in a subject. The method may comprise administering the particle and/or composition to the subject. Exemplary viruses include, but are not limited to, coronaviruses (e.g., severe acute respiratory syndrome (SARS) coronavirus (SARS-CoV), severe acute respiratory syndrome coronavirus 2 (SARS-CoV-2), and/or Middle East respiratory syndrome (MERS) coronavirus (MERS-CoV)), influenza virus, adenoviruses, respiratory syncytical viruses, dengue viruses (e.g., dengue fever), and/or parainfluenza viruses. In some embodiments, a particle, composition and/or method of the present invention treats and/or prevents a coronavirus such as SARS-CoV-2.

A particle and/or composition of the present invention may be administered in any suitable manner. In some embodiments, a composition of the present invention is formulated and/or configured for an intended mode of administration. A particle and/or composition of the present invention may be orally, topically, and/or parenterally administered to a subject. In some embodiments, administering a particle and/or composition of the present invention is via inhalation (e.g., a subject inhales the particle and/or composition or an atomized or vaporized form of the particle and/or composition is inhaled). In some embodiments, the composition is in the form of a liquid, optionally an aqueous suspension comprising a plurality of particles of the present invention. In some embodiments, the composition is in the form of a lotion, cream, ointment, or solid. In some embodiments, prior to administering, a particle and/or composition of the present invention is combined (e.g., brewed such as one would to prepare tea) with heated water (e.g., water at a temperature in a range of about 60° C., 65° C., 70° C., or 75° C. to about 80° C., 85° C., 90° C., 95° C., or 100° C.) for about 1, 2, 4, or 6 minutes to about 8, 10, 12, 15, or 20 minutes, and then the particle and/or composition in water (e.g., heated water) is ingested and/or topically administered. In some embodiments, administering to a subject the particle and/or composition in heated water directs and/or aids in directing the particle and/or composition to the respiratory system (e.g., lungs) of a subject and/or increases effectiveness in the respiratory system of a subject.

In some embodiments, administering of the particle and/or composition to the subject comprises administering gold to the subject in an amount of about 1, 2, 4, 6, 8, 10, 15, 20, 25, 30, 35, 40, 45, or 50 microgram(s) to about 55, 60, 65, 70, 75, 80, 85, 90, 95, 100, 150, 200, 250, 300, 350, or 400 micrograms. In some embodiments, gold is administered to the subject in an amount of about 1, 2, 4, 6, 8, 10, 15, 20, 25, 30, 35, 40, 45, 50, 55, 60, 65, 70, 75, 80, 85, 90, 95, 100, 150, 200, 250, 300, 350, or 400 micrograms. In some embodiments, administering of the composition comprises administering gold to the subject in an amount of about 1, 2, 4, 6, 8, 10, 15, 20, 25, 30, 35, 40, 45, or 50 microgram(s) of gold per mL of the composition to about 55, 60, 65, 70, 75, 80, 85, 90, 95, 100, 150, 200, 250, 300, 350, or 400 micrograms of gold per mL of the composition. In some embodiments, gold is administered to the subject in an amount of about 1, 2, 4, 6, 8, 10, 15, 20, 25, 30, 35, 40, 45, 50, 55, 60, 65, 70, 75, 80, 85, 90, 95, 100, 150, 200, 250, 300, 350, or 400 micrograms of gold per mL of the composition.

A method of the present invention may comprise administering the particle and/or composition to the subject one or more (e.g., 1, 2, 3, 4, or more) times a day. In some embodiments, a composition of the present invention is administered to the subject once daily or twice daily (e.g., at morning and at night). In some embodiments, the dose of the particle and/or composition administered provides about 1, 2, 4, 6, 8, 10, 15, 20, 25, 30, 35, 40, 45, or 50 microgram(s) to about 55, 60, 65, 70, 75, 80, 85, 90, 95, 100, 150, 200, 250, 300, 350, or 400 micrograms of gold that is administered to the subject per dose. In some embodiments, the particle and/or composition is administered as needed or as desired by the subject. In some embodiments, the particle and/or composition is administered to the subject at least 1, 2, 3, 4, 5, 6, 7, 8, or more times per week and/or month. In some embodiments, the particle and/or composition is administered to the subject at least once daily for an extended period of time (e.g., 1, 2, 3, 4, 5, 6, or more week(s) and/or month(s)) and/or until a desired effect is achieved (e.g., a therapeutic effect).

In some embodiments, a method of the present invention reduces pain; reduces inflammation; enhances sleep (e.g., increases length of total sleep and/or increases REM time); increases apoptosis of diseased cells and/or increases the rate of apoptosis for diseased cells (e.g., virally infected cells and/or cancer cells); decreases apoptosis of healthy cells and/or decreases the rate of apoptosis for healthy cells; increases cell and/or subject life span; decreases recovery time after exertion, injury and/or illness; enhances mental clarity (e.g., reduces fogginess); enhances memory; decreases drowsiness; increases attention and/or attention span; enhances respiration; decreases anxiety; enhances stamina; enhances appearance (e.g., enhances skin and/or hair appearance), and/or reduces relapse time (e.g., of symptoms, outbreaks, and/or lesions) in a subject. In some embodiments, a particle and/or composition of the present invention may pass and/or enter into a circulatory system of a subject such as through intracellular passages. The particle and/or one or more component(s) of the composition may be adsorbed and/or dissolved in a fluid (e.g., blood) of the subject and/or may be internalized (e.g., via endocytosis) by a cell of the subject. In some embodiments, the oleo-gum resin and/or derivative thereof and/or an active ingredient may be delivered to the subject, internalized by a cell of the subject, and/or released from a particle of the present invention.

In some embodiments, administration of a particle and/or composition of the present invention enhances cellular uptake of the oleo-gum resin and/or derivative thereof and/or an active ingredient by gut microbiome of the subject and/or may increase conversion of active metabolites from the oleo-gum resin and/or derivative thereof and/or the active ingredient. The active metabolites may be adsorbed and/or dissolved in a fluid (e.g., blood) of the subject and/or may be internalized (e.g., via endocytosis) by a cell of the subject. In some embodiments, administration of a particle and/or composition of the present invention does not interfere with, adversely affect, and/or reduce the effectiveness of an active ingredient (e.g., a therapeutic such as an antiviral or anti-inflammatory agent) that is also administered to the subject.

In some embodiments, administration of a particle and/or composition of the present invention to a subject along with an active ingredient directs the beneficial properties (e.g., therapeutic properties) to a particular location in and/or on the subject. For example, administration of a particle and/or composition of the present invention to a subject along with cinnamon (e.g., in the composition or separately administered) may direct the beneficial properties to the bladder and/or kidneys of the subject.

In some embodiments, administration of a particle and/or composition of the present invention may provide for microbiome balancing in the subject such as through selective anti-microbial properties of frankincense or a derivative thereof and/or myrrh or a derivative thereof. In some embodiments, a particle of the present invention may be absorbed by certain microbes present in and/or on a subject, optionally through endocytosis of the particle in the gut and/or intestinal microbiome. In some embodiments, administration of the particle and/or composition may result in death and/or stagnation of certain toxic microbes, which may thereby purify or cleanse the microbiome by reducing or eliminating toxins and/or toxin producing microbes.

Embodiments of the present invention may be further described by the below clauses.

Clause 1. A particle comprising gold and an oleo-gum resin and/or a derivative thereof.

Clause 2. The particle of clause 1, wherein the oleo-gum resin and/or derivative thereof is obtained from a tree of the genus selected from the group consisting of *Boswellia, Commiphora,* and any combination thereof.

Clause 3. The particle of clause 1 or 2, wherein the oleo-gum resin and/or derivative thereof is selected from frankincense or a derivative thereof, myrrh or a derivative thereof, and any combination thereof.

Clause 4. The particle of any one of clauses 1-3, wherein the particle comprises a terpenoid (e.g., a boswellic acid, a monoterpenoid, a diterpenoid, a triterpenoid, sesquiterpenoid, a pentacyclic triterpenoid, a furano-sesquiterpenoid, etc.), a steroid (e.g., a natural steroid), a flavonoid, a terpene, a guggulsterol, a guggulsterone, a lignan, a sugar, an amino acid, a polypeptide, a carbohydrate, a fatty alcohol, a fatty ester, a sterol (e.g., a natural sterol), a precursor of any of the foregoing, and any combination thereof.

Clause 5. The particle of any one of clauses 1-4, wherein the particle comprises frankincense or a derivative thereof in an amount of about 40% to about 85% by weight of the oleo-gum resin and/or derivative thereof and/or myrrh or a derivative thereof in an amount of about 10% to about 50% by weight of the oleo-gum resin and/or derivative thereof.

Clause 6. The particle of any one of clauses 1-5, wherein the particle comprises a core having an outer surface, and wherein the core comprises gold and optionally the oleo-gum resin and/or derivative thereof.

Clause 7. The particle of clause 6, wherein the outer surface comprises the oleo-gum resin and/or derivative thereof.

Clause 8. The particle of any one of clauses 1-7, wherein the particle is a nanoparticle.

Clause 9. The particle of any one of clauses 1-8, wherein the particle has a diameter of about 5, 10, or 20 nm to about 30, 40, 50, 100, 250, or 500 nm.

Clause 10. The particle of any one of clauses 6-9, wherein the core has a diameter of about 5, 10, or 20 nm to about 30, 40, 50 or 100 nm.

Clause 11. The particle of any one of clauses 1-10, wherein the particle is a nanosphere, nanorod, nanoshell, nanoprism, nanocluster, nanocage, or nanostar Clause 12. The particle of any one of clauses 1-11, further comprising an active ingredient (e.g., a botanical, supplement, vitamin, and/or therapeutic agent), silicon and/or a silicon containing compound.

Clause 13. The particle of any one of clauses 1-12, wherein the particle is soluble in water or suspended in water.

Clause 14. A composition comprising the particle of any one of clauses 1-13.

Clause 15. The composition of clause 14, further comprising water.

Clause 16. The composition of any one of clauses 14-15, wherein the composition has a viscosity in a range of about 0.001 poise to about 10 poise at room temperature and pressure and/or a density in a range of about 0.95 g/cm$^3$ to about 1.5 g/cm$^3$ at room temperature and pressure.

Clause 17. A method of making a particle, the method comprising: combining an oleo-gum resin and/or a derivative thereof and a solution comprising soluble gold to form a mixture; and forming a particle from the mixture, wherein the particle comprises gold and the oleo-gum resin and/or a derivative thereof.

Clause 18. The method of clause 17, wherein the oleo-gum resin and/or derivative thereof is a raw oleo-gum resin (e.g., in the form of a powder or tear).

Clause 19. The method of any one of clauses 17-18, wherein the soluble gold is chloroauric acid.

Clause 20. The method of any one of clauses 17-19, further comprising preparing the soluble gold by acidifying an aqueous composition comprising a gold salt.

Clause 21. The method of any one of clauses 17-20, further comprising preparing the soluble gold by dissolving solid gold using aqua regia (i.e., a mixture of nitric acid and hydrochloric acid).

Clause 22. The method of any one of clauses 17-21, wherein the combining step comprises combining the oleo-gum resin and/or derivative thereof and soluble gold in a weight ratio of about 2000:1 to about 100:1 (oleo-gum resin and/or derivative thereof:soluble gold).

Clause 23. The method of any one of clauses 17-22, wherein the combining step comprises heating water to a temperature in a range of about 40° C. to about 150° C. to form heated water, and adding the oleo-gum resin and/or derivative thereof and/or soluble gold to the heated water to form the mixture.

Clause 24. The method of any one of clauses 17-23, wherein the combining step comprises heating water to a temperature in a range of about 40° C. to about 150° C. to form heated water, and adding the oleo-gum resin and/or derivative thereof to the heated water to form a heated oleo-gum resin composition, and adding the soluble gold to the heated oleo-gum resin composition to form the mixture.

Clause 25. The method of any one of clauses 17-24, further comprising heating the solution and/or mixture to a temperature in a range of about 40° C. to about 150° C.

Clause 26. A particle prepared according to the method of any one of clauses 17-25.

Clause 27. A method of treating and/or preventing a disease, disorder, or condition in a subject in need thereof, the method comprising: administering to the subject the particle of any one of clauses 1-13 or 26, or the composition of any one of clauses 15-16, or a particle prepared according to the method of any one of clauses 17-25, thereby treating and/or preventing the disease, disorder, or condition in a subject.

Clause 28. The method of clause 27, wherein the particle increases bioavailability of the oleo-gum resin and/or derivative thereof in the subject compared to bioavailability of the oleo-gum resin and/or derivative thereof administered to the subject alone.

Clause 29. The method of clause 27 or 28, wherein the administering comprises orally, topically, and/or parenterally administering the particle or composition to the subject.

Clause 30. The method of any one of clauses 27-29, wherein the administering comprises the subject inhaling the particle or composition or an atomized or vaporized form thereof.

Clause 31. The method of any one of clauses 27-30, wherein the particle or composition is administered to the subject at a dose that achieves an additive effect.

Clause 32. The method of any one of clauses 27-31, wherein the particle or composition is administered to the subject at a dose that achieves a synergistic effect.

Clause 33. The method of any one of clauses 27-32, wherein the particle or composition are in the form of a liquid, gel, cream, ointment, or solid.

Clause 34. The method of any one of clauses 27-33, wherein the particle or composition are in the form of a capsule or tablet.

Clause 35. The method of any one of clauses 27-34, further comprising administering an active ingredient (e.g., a botanical, supplement, vitamin, therapeutic agent) to the subject.

Clause 36. The method of any one of clauses 27-35, wherein administering the active ingredient comprises administering the active ingredient concurrently with the particle or composition, optionally wherein the composition comprises the particle and the active ingredient.

Clause 37. The method of any one of clauses 27-36, wherein administering the active ingredient comprises separately administering the active ingredient and the particle or composition.

Clause 38. The method of any one of clauses 27-37, wherein the particle increases bioavailability of the active ingredient in the subject compared to bioavailability of the active ingredient administered to the subject alone.

Clause 39. The method of any one of clauses 27-38, wherein the particle and active ingredient are administered to the subject at a dose that achieves an additive effect.

Clause 40. The method of any one of clauses 27-39, wherein the particle and active ingredient are administered to the subject at a dose that achieves a synergistic effect.

Clause 41. The method of any one of clauses 27-40, wherein the method reduces pain; reduces inflammation; improves sleep; increases apoptosis of diseased cells and/or increases the rate of apoptosis for diseased cells (e.g., virally infected cells and/or cancer cells); decreases apoptosis of healthy cells and/or decreases the rate of apoptosis for healthy cells; increases cell and/or subject life span; decreases recovery time after exertion, injury or illness; improves mental clarity; improves memory; decreases drowsiness; increases attention; improves respiration; decreases anxiety; improves stamina; and/or improves appearance.

Clause 42. The method of any one of clauses 27-41, wherein the administering comprises administering gold via the particle or composition in an amount of about 1, 2, 4, 6, 8, 10, 15, 20, 25, 30, 35, 40, 45, or 50 microgram(s) to about 55, 60, 65, 70, 75, 80, 85, 90, 95, 100, 150, 200, 250, 300, 350, or 400 micrograms.

The present invention is explained in greater detail in the following non-limiting examples.

EXAMPLES

Example 1

Chloroauric acid was prepared by dissolving a gold chloride salt (e.g., sodium tetrachloroaurate ($NaAuCl_4$), potassium ($KAuCl_4$) or magnesium ($Mg(AuCl_4)_2$) in water and then acidifying the solution with HCl acid in a 1:1 molar ratio.

Example 2

Chloroauric acid was prepared by dissolving solid metallic gold in a dissolving solution made of 5.23 parts (liquid volume) concentrated hydrochloric acid (12 Molar or 37% HCl) mixed with one part (liquid volume) concentrated nitric acid (15.7 Molar or 70% wt/wt $HNO_3$). Add to every 1 L of dissolving solution was 500 grams (17.6 ounces) of 24 karat gold. The reaction was continued until the liquid was translucent yellow and the action on the solid gold was discontinued.

Example 3

Gold particles with frankincense and myrrh were prepared. Chloroauric acid was obtained from commercial sources or was prepared such as described in Example 1 or 2.

A chloroauric acid solution was mixed with raw (powdered or teared) frankincense and myrrh in the presence of water at room temperature to produce particles including frankincense and myrrh. At room temperature, the process took many hours to several days.

Example 4

Gold particles with frankincense and myrrh were prepared. Chloroauric acid was obtained from commercial sources or was prepared such as described in Example 1 or 2.

Water was heated to about 100 degrees Celsius, until a rolling boil is observed. Powdered or teared frankincense and myrrh were each added to the boiling water. When the mixture regained the rolling boil and reached a consistency of smooth bubbling tar or hot bubble gum and no more powder or tears are observed in their natural form, then chloroauric acid was added. Within a few seconds the mixture changed from a turbid light brown color to a dark purple color indicating the presence and creation of nanoparticles. Cooling the mixture resulted in the precipitation of insoluble frankincense and myrrh components. Insoluble materials can be filtered out if desired.

Example 5

The composition including the particles as prepared in Example 3 or Example 4, optionally filtered, (referred to as "GFM") was administered to each of subjects as described below. Unless otherwise stated, each subject was administered twice daily about 0.5 mL to about 1 mL of the composition having about 80 micrograms of gold/mL.

Subject A—Male, age mid 50's, had experienced knee pain since his late teens preventing him from running as exercise. He also had chronic pain in the neck that flared up upon certain activities such as playing golf or looking up for a sustained time. Two weeks after oral administration of GFM both knee and neck pain disappeared. He resumed running after a 30+ year inability. So long as he maintains consumption the pain has stayed at bay.

Subject B—Male, age early 50's, had suffered a stroke 18 months previous. The stroke left him with an inability to read, some speech anomalies, as well as a number of neuropathic symptoms including pain and numbness in his extremities. After taking GFM orally for a month he realized his neuropathic pain was considerably less and numbness had decreased especially in his hands. After 3 months he had such foot pain relief he was able to begin walking for exercise. After 6 months he noticed his speech patterns improving to the point it was difficult to tell he had a stroke. Within a year he began reading again.

Subject C—Female, age early 70's, suffers from periodic psoriasis on her hands, neck, and arms. She was unable to obtain relief through traditional medical avenues. She applied GFM topically and found it caused the psoriatic outbreak to diminish rapidly. It also seems to lessen the times between outbreaks.

Subject D—Female, age mid 40's, had experienced pain in her right shoulder since a teenager. Oral GFM worked rapidly and she is pain free so long as she takes two doses a day.

Subject E—Male, age late 50's, had irritable bowel syndrome (IBS) since his youth constantly fluctuating between diarrhea and constipation. Within a week of taking GFM orally he noticed he was quite astonishingly regular. This has now been the case for extended period of time.

Subject F—Female, age late 60's, tripped and broke her wrist the previous year and had residual pain in the wrist and hand. After oral consumption of GFM she no longer experiences the pain.

Subject G—Female, age 25, suffered with bad knee and ankle pain. Difficulty exercising. Knee and ankle pain gone since taking GFM.

Subject H—Female, age late 50's, general knee pain and arthritis pain in hand and finger joints. Knee pain and arthritis pain gone after 3 to 4 days starting GFM.

Subject I—Male, age late 50's, knee and back pain for many years. Within a week of taking GFM, knee pain was gone, but little impact on back pain.

Subject J—Male, age mid 50's, increased stamina after 1 week of taking GFM

Subject K—Male, age mid 20's increase in stamina, waking up early feeling much better, no morning "brain fog".

Example 6

A drop of GFM was placed on a silicon wafer and allowed to evaporate by air until dry. Scanning electron microscope (SEM) images were then taken of the dried GFM sample on the silicon wafer (FIGS. 1-4).

FIG. 1 is a SEM image taken at a magnification of 1,500× showing that the dried GFM has formed a film on the silicon wafer. While there may be a thin GFM layer in the light gray region, the light gray region in FIG. 1 appears to be primarily the silicon wafer and the dark gray region in FIG. 1 is the GFM film on the wafer. It appears that GFM stuck to itself better than to the silicon wafer.

Figure 2:
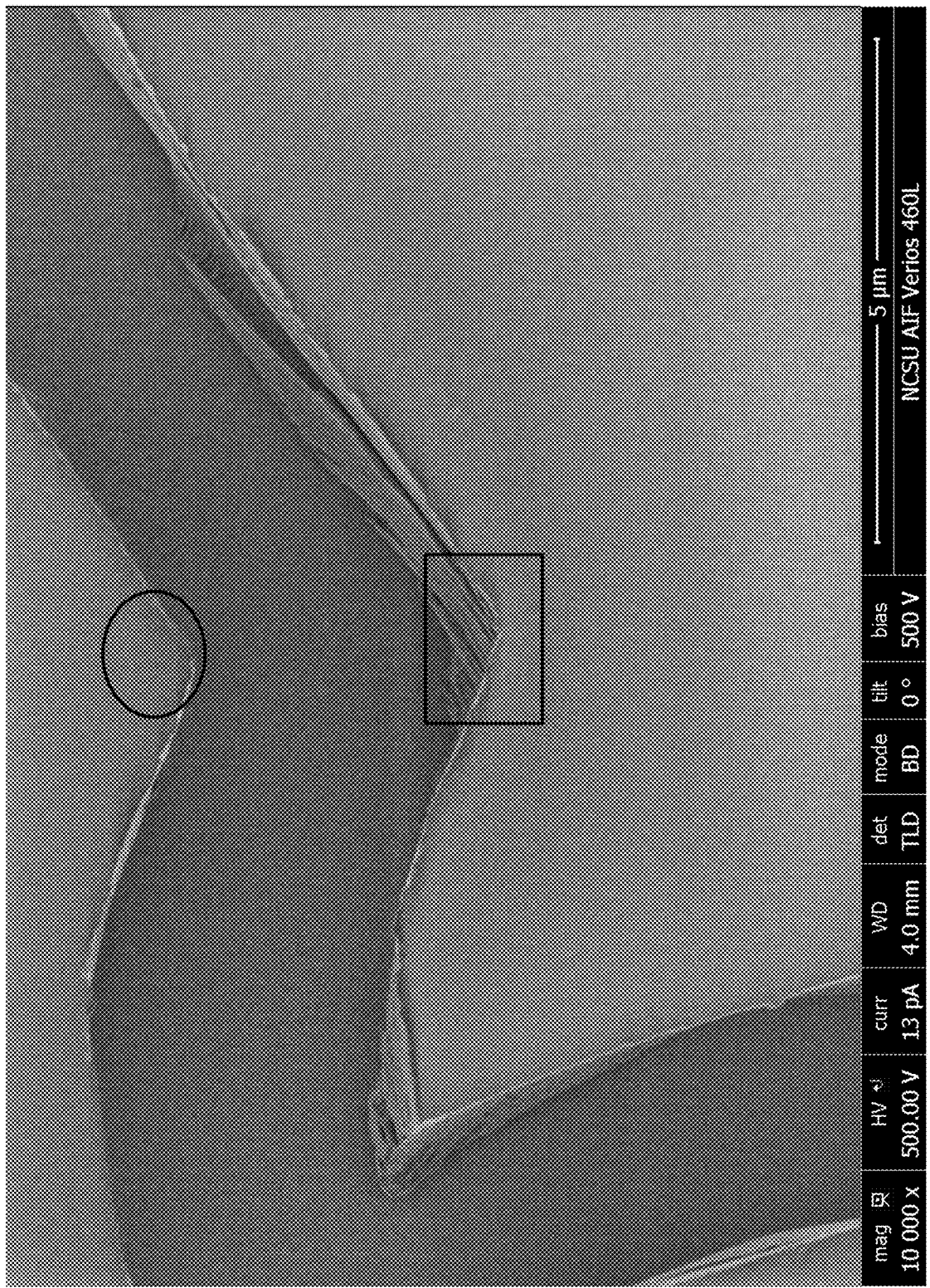

FIG. 2 is a SEM image taken at a magnification of 10,000× and this image has the contrast reversed compared to FIG. 1 due to the way the electrons interact with GFM. For SEM, at very low energies (e.g., 1 keV or less), the contrast can be different than what one would expect at higher energies. In general, an SEM image is a map of the electron emission coefficient of the sample. The boxed region shown in FIG. 1 is approximately the region magnified in FIG. 2. As can be seen in FIG. 2, there is some material in the valley formed by the film since silicon wafers are polished and are very smooth.

Figure 3:
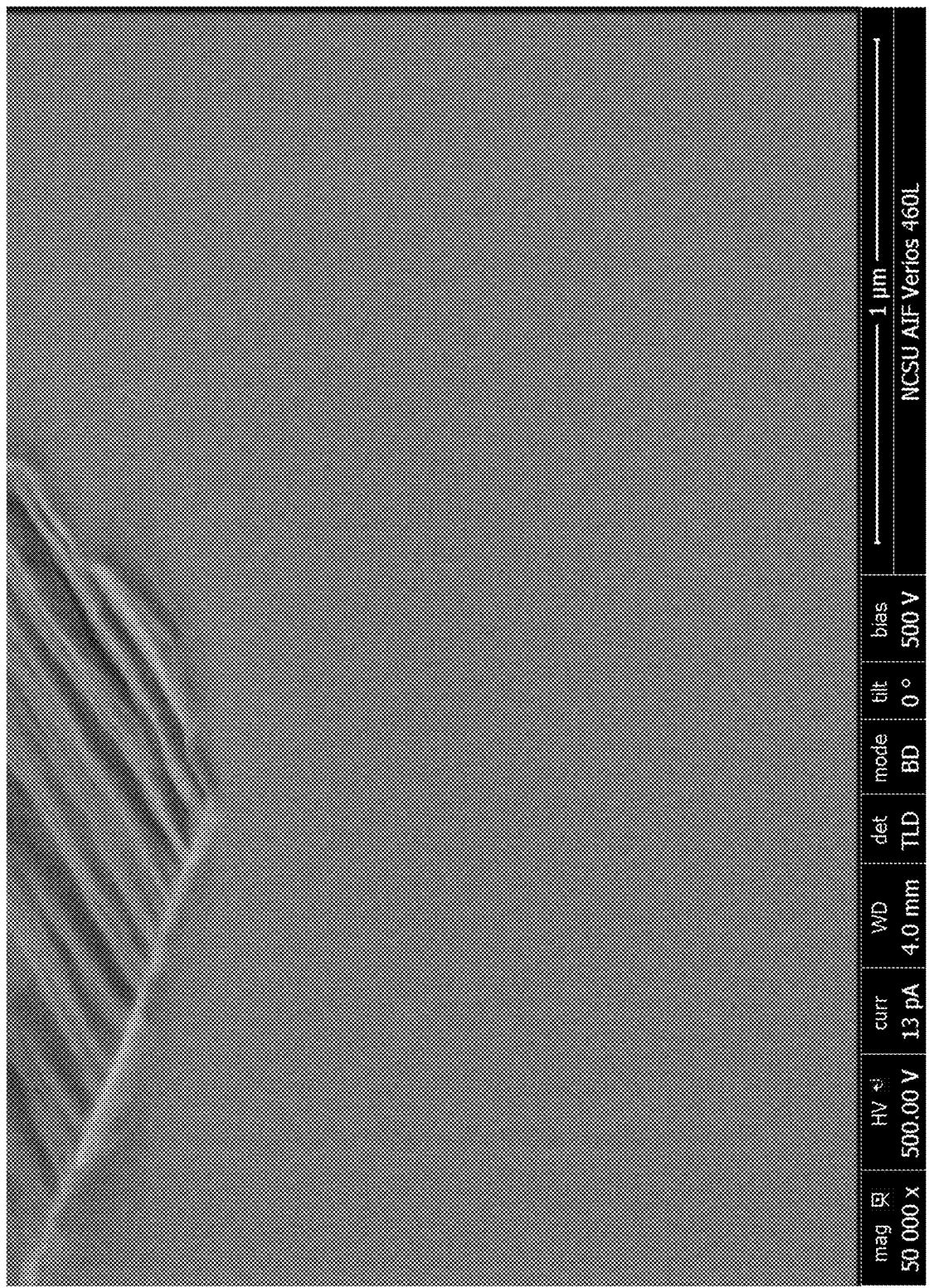

FIG. 3 is a SEM image taken at a magnification of 50,000×. The boxed region shown in FIG. 2 is approximately the region magnified in FIG. 3. As can be seen in FIG. 3, filaments (e.g., rods) can be seen in the dried GFM film and no particles are observed in the dried GFM film.

Figure 4:
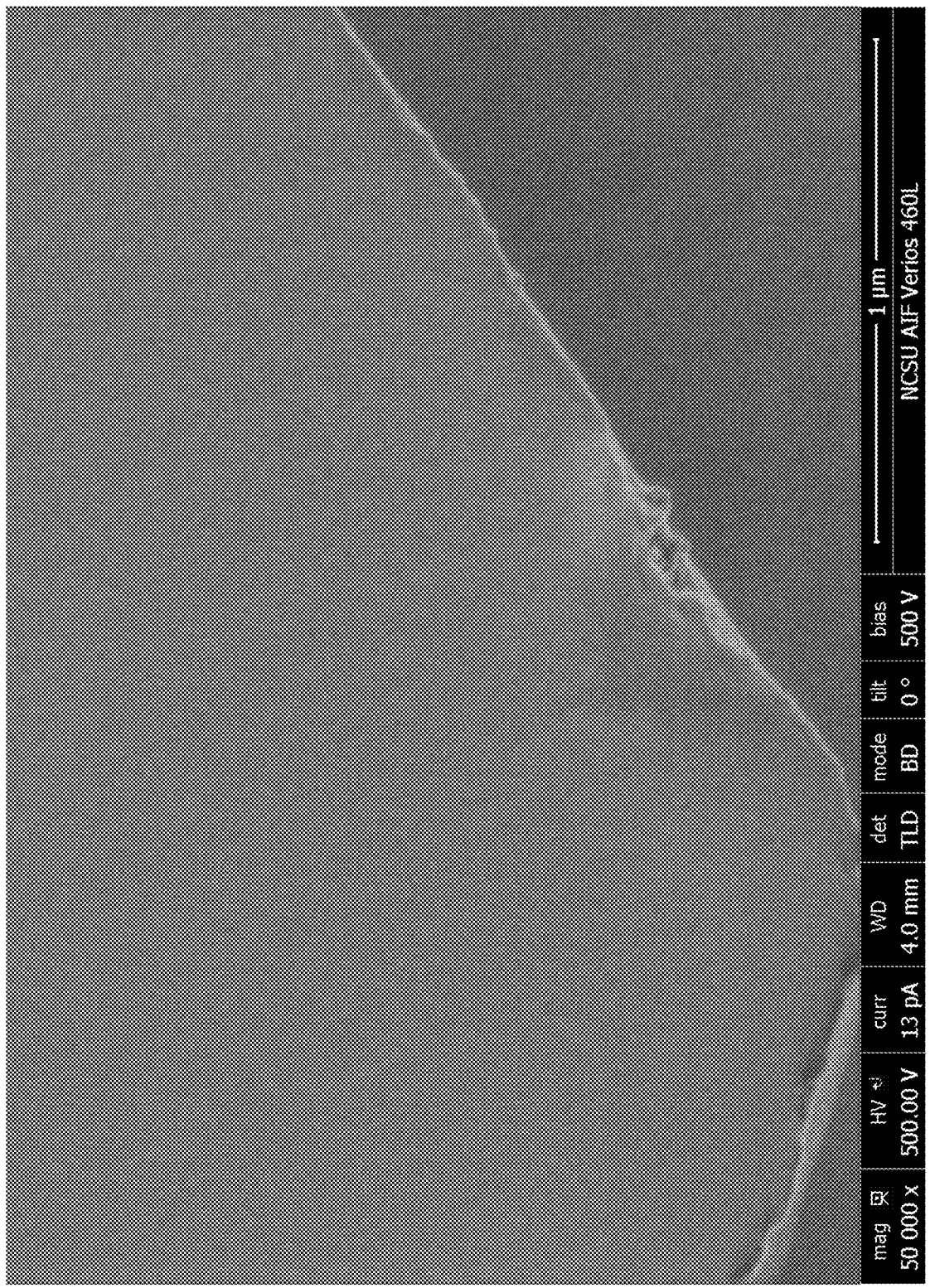

FIG. 4 is a SEM image taken at a magnification of 50,000×. The circled region shown in FIG. 2 is approximately the region magnified in FIG. 4.

Example 7

Figure 5:
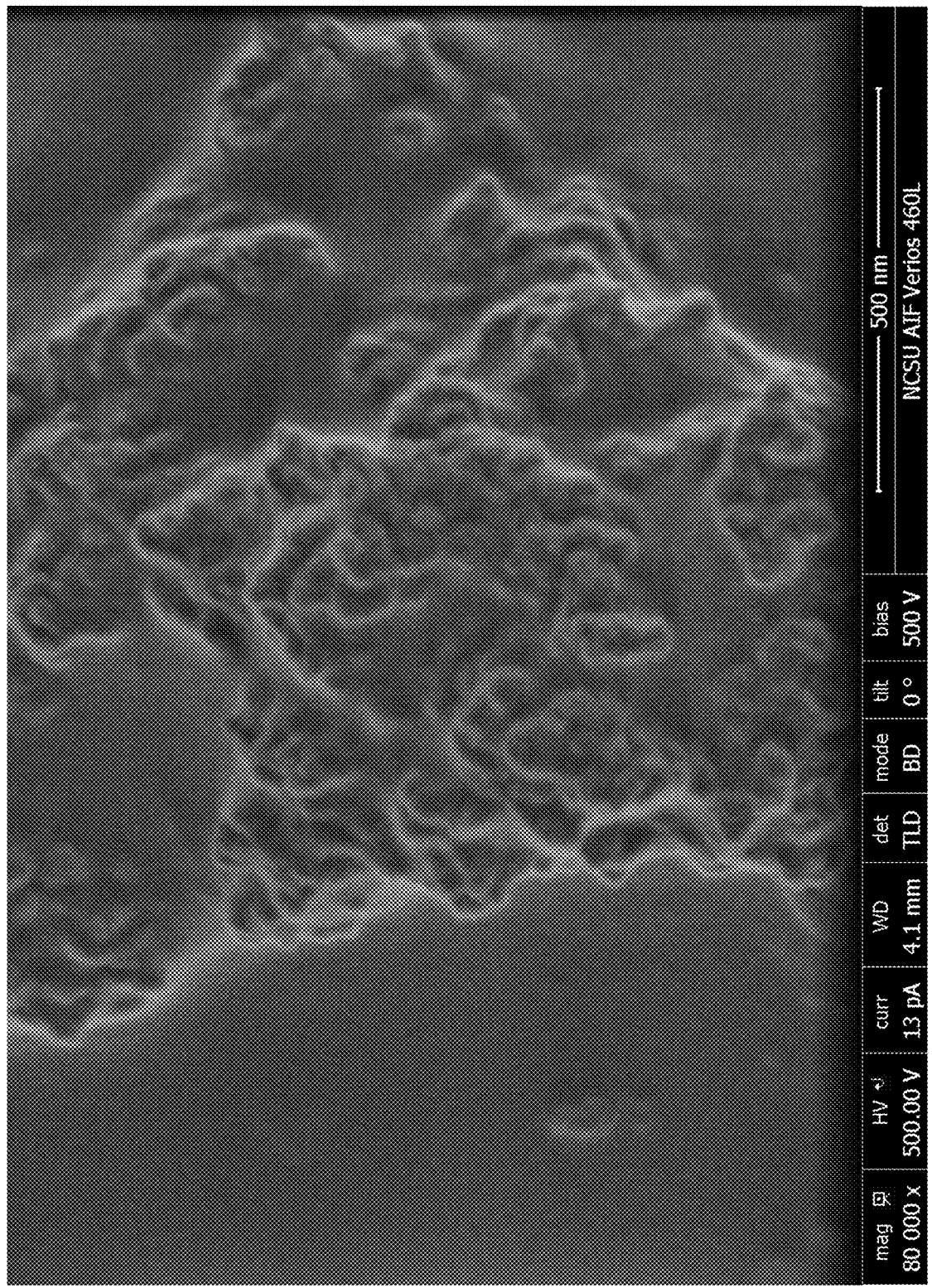
Figure 6:
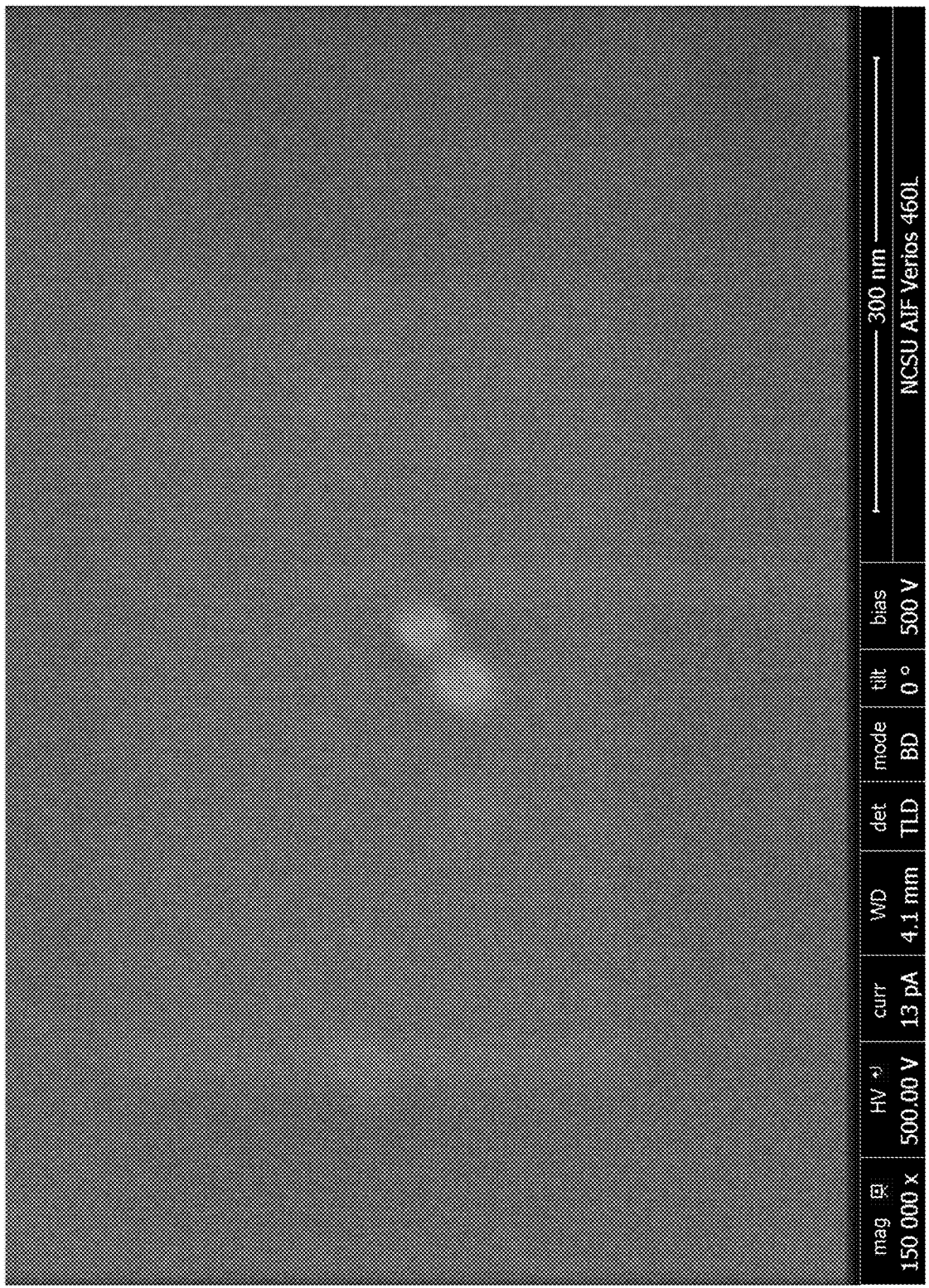

GFM was diluted 100-fold with water and then was placed on a silicon wafer and allowed to evaporate by air until dry. As can be seen in FIG. 5, clumps of particles are visible and not rods or filaments. FIG. 6 demonstrates that the individual particles, which appear as light gray circles, have a diameter of about 21 nm to about 53 nm. While not wishing to be bound to any particular theory, the concentration of GFM particles may affect the formation of GFM structures (e.g., nanostructures).

The foregoing is illustrative of the present invention, and is not to be construed as limiting thereof. The invention is defined by the following claims, with equivalents of the claims to be included therein.

That which is claimed is:

1. A nanoparticle comprising gold and an oleo-gum resin, wherein the oleo-gum resin comprises frankincense and myrrh,
wherein the frankincense is present in an amount of about 40% to about 85% by weight of the oleo-gum resin and the myrrh is present in an amount of about 10% to about 50% by weight of the oleo-gum resin,
wherein the particle is devoid of a gold surface in direct contact with a citrate ion, and
wherein the frankincense is obtained from a *Boswellia* species and the myrrh is obtained from a *Commiphora* species.

2. The nanoparticle of claim 1, wherein the oleo-gum resin consists of frankincense and myrrh.

3. The nanoparticle of claim 1, wherein the frankincense and/or myrrh comprise a terpenoid, a steroid, a flavonoid, a terpene, a guggulsterol, a guggulsterone, a lignan, a sugar, an amino acid, a polypeptide, a carbohydrate, a fatty alcohol, a fatty ester, a sterol, a precursor of any of the foregoing, and any combination thereof.

4. The nanoparticle of claim 1, wherein the nanoparticle comprises the frankincense in an amount of about 50% to about 70% by weight of the oleo-gum resin and the myrrh in an amount of about 30% to about 50% by weight of the oleo-gum resin.

5. The nanoparticle of claim 1, wherein the nanoparticle comprises a core having an outer surface, and wherein the core comprises gold and optionally the oleo-gum resin.

6. The nanoparticle of claim 1, wherein the nanoparticle has a diameter of about 21 nm to about 500 nm.

7. The nanoparticle of claim 1, wherein the nanoparticle is a nanosphere, nanorod, nanoshell, nanoprism, nanocluster, nanocage, or nanostar.

8. The nanoparticle of claim 1, further comprising an active ingredient, silicon and/or a silicon containing compound.

9. The nanoparticle of claim 1, wherein the nanoparticle is soluble in water or suspended in water.

10. A composition comprising the nanoparticle of claim 1.

11. The composition of claim 10, further comprising water.

12. The composition of claim 10, wherein the composition has a viscosity in a range of about 0.001 poise to about 10 poise at room temperature and pressure and/or a density in a range of about 0.95 $g/cm^3$ to about 1.5 $g/cm^3$ at room temperature and pressure.

13. A method of making the nanoparticle of claim 1, the method comprising:
combining an oleo-gum resin comprising frankincense and myrrh and a solution comprising soluble gold to form a mixture; and
forming the nanoparticle from the mixture.

14. The method of claim 13, wherein the oleo-gum resin is a raw oleo-gum resin.

15. The method of claim 13, wherein the combining step comprises combining the oleo-gum resin and soluble gold in a weight ratio of about 2000:1 to about 100:1 (oleo-gum resin:soluble gold).

16. A nanoparticle prepared according to the method of claim 13.

17. A method of ameliorating a symptom of a disease, disorder, or condition in a subject in need thereof, the method comprising:
administering to the subject a therapeutically effective amount of the nanoparticle of claim 1,
wherein the disease, disorder, or condition is pain, inflammation, an infection, cancer, psoriasis, or irritable bowel syndrome.

* * * * *

UNITED STATES PATENT AND TRADEMARK OFFICE
CERTIFICATE OF CORRECTION

| | | |
|---|---|---|
| PATENT NO. | : 11,752,108 B2 | |
| APPLICATION NO. | : 17/203138 | |
| DATED | : September 12, 2023 | |
| INVENTOR(S) | : Blonshine et al. | |

It is certified that error appears in the above-identified patent and that said Letters Patent is hereby corrected as shown below:

On the Title Page

Item (56), OTHER PUBLICATIONS: Please correct "SHUKLA et al. "Soybeans as a Phytochemical Reservoir for the Production and Stabilization of Biocompatible Gold Manoparticles" Small, 4(9): 1425-1436 (2008)" to read --SHUKLA et al. "Soybeans as a Phytochemical Reservoir for the Production and Stabilization of Biocompatible Gold Nanoparticles" Small, 4(9):1425-1436 (2008)--

In the Specification

Column 11, Line 12: Please correct "5-pregnenol one," to read --5-pregnenolone,--

Column 11, Line 12: Please correct "δ5 -pregnene-3β-ol-20-one," to read --δ5-pregnene-3β-ol-20-one,--

Column 16, Line 7: Please correct "gold II)" to read --gold (I)--

Signed and Sealed this
Sixteenth Day of July, 2024

Katherine Kelly Vidal
*Director of the United States Patent and Trademark Office*